US009447026B2

(12) United States Patent
Bunker

(10) Patent No.: US 9,447,026 B2
(45) Date of Patent: *Sep. 20, 2016

(54) BICYCLIC ANALGESIC COMPOUNDS

(71) Applicant: KALYRA PHARMACEUTICALS, INC., San Diego, CA (US)

(72) Inventor: Kevin Duane Bunker, San Diego, CA (US)

(73) Assignee: Kalyra Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/439,636

(22) PCT Filed: Mar. 6, 2014

(86) PCT No.: PCT/US2014/021038
§ 371 (c)(1),
(2) Date: Apr. 29, 2015

(87) PCT Pub. No.: WO2014/149819
PCT Pub. Date: Sep. 25, 2014

(65) Prior Publication Data
US 2016/0016892 A1    Jan. 21, 2016

Related U.S. Application Data

(60) Provisional application No. 61/781,580, filed on Mar. 14, 2013.

(51) Int. Cl.
| | |
|---|---|
| *C07C 233/52* | (2006.01) |
| *C07C 217/52* | (2006.01) |
| *C07C 233/06* | (2006.01) |
| *C07C 233/23* | (2006.01) |
| *C07C 233/41* | (2006.01) |
| *C07C 235/74* | (2006.01) |
| *A61K 31/13* | (2006.01) |
| *A61K 31/16* | (2006.01) |
| *A61K 31/216* | (2006.01) |
| *A61K 31/222* | (2006.01) |
| *A61K 31/235* | (2006.01) |
| *A61K 45/06* | (2006.01) |
| *A61K 31/14* | (2006.01) |
| *A61K 31/215* | (2006.01) |
| *A61K 31/22* | (2006.01) |
| *C07C 211/62* | (2006.01) |

(52) U.S. Cl.
CPC ............ *C07C 233/52* (2013.01); *A61K 31/13* (2013.01); *A61K 31/14* (2013.01); *A61K 31/16* (2013.01); *A61K 31/215* (2013.01); *A61K 31/216* (2013.01); *A61K 31/22* (2013.01); *A61K 31/235* (2013.01); *A61K 45/06* (2013.01); *C07C 211/62* (2013.01); *C07C 217/52* (2013.01); *C07C 233/06* (2013.01); *C07C 233/23* (2013.01); *C07C 233/41* (2013.01); *C07C 235/74* (2013.01); *C07C 2102/38* (2013.01)

(58) Field of Classification Search
CPC . C07C 233/52; C07C 217/52; C07C 233/06; C07C 233/23; C07C 233/41; C07C 235/74; A61K 31/13; A61K 31/16; A61K 31/216; A61K 31/222; A61K 31/235; A61K 45/06
See application file for complete search history.

(56) References Cited

U.S. PATENT DOCUMENTS

| | | |
|---|---|---|
| 5,262,417 A | 11/1993 | Gammill et al. |
| 2013/0029987 A1 | 1/2013 | Bennett et al. |
| 2014/0275245 A1 | 9/2014 | Bunker |
| 2016/0075654 A1 | 3/2016 | Bunker et al. |

FOREIGN PATENT DOCUMENTS

WO    WO 2012/145569    10/2012

OTHER PUBLICATIONS

Lee, I. O.; Kong, M. H.; Kim, N. S.; Choi, Y. S.; Lim, S. H.; Lee, M. K. Acta. Anaesthesiologica Sinica 2000, 38, 59-64.*
Tjolsen, A.; Berge, O. G.; Hunskaar, S.; Rosland, J. H.; Hole, K. Pain 1992, 51, 5-17.*
Vahidy, W. H.; Ong, W. Y.; Farooqui, A. A.; Yeo, J. F. Exp. Brain Res. 2006, 174, 781-785.*
Henry, J. L. J. Orofac. Pain 2004, 18, 306-310.*
Vissers, K. C. P.; Greenen, F.; Biermans, R.; Meert, T. F. Pharmacology, Biochemistry and Behaviour 2006, 84, 479-486.*
Wheeler-Aceto, H.; Cowan, A. Psychopharmacology (Berl) 1991, 104, 35-44.*
Sufka, K. J.; Watson, G. S.; Nothdurft, R. E.; Mogil, J. S. Eur. J. Pain 1998, 2, 351-358.*
Adcock, W., et al., "Transmission of polar substituent effects across the bicyclo[1.1.1]pentane ring system as monitored by $^{19}$F NMR shifts" *Magn. Reson. Chem.*(2000) 38:115-122.
Adcock, W., et al., "Computation and analysis of 19F substituent chemical shifts of some bridgehead-substituted polycyclic alkyl fluorides" *Magn. Reson. Chem.*(2003) 41(7):503-508.
Adcock, W., "A DFT-GIAO and DFT-NBO study of polar substituent effects on NMR $^{17}$O chemical shifts in some rigid polycyclic alkanes" *J. Phys. Org. Chem.*(2011) 24:492-498.
Annese, C., et al., "Oxyfunctionalization of Non-Natural Targets by Dioxiranes. 6. On the Selective Hydroxylation of Cubane" *Org. Lett.*(2009) 11(16):3574-3577.
Applequist, D.E., et al., "Polar Substituent Effects in 1,3-Disubstituted Bicyclo[1.1.1]pentanes" *J. Org. Chem.*(1982) 47:4985-4995.

(Continued)

*Primary Examiner* — Sahar Javanmard
(74) *Attorney, Agent, or Firm* — Knobbe Martens Olson & Bear LLP

(57) ABSTRACT

Analgesic compounds for treatment of pain or fever that include a bicyclopentane moiety linked to an amine, combinations of the compounds with opioid analgesic drugs, and methods for treating pain or fever by administering a compound described herein.

74 Claims, 10 Drawing Sheets

(56) References Cited

OTHER PUBLICATIONS

Arnone A., et al., "Highly Enantiospecific Oxyfunctionalization of Nonactivated Hydrocarbon Sites by Perfluoro-cis-2-n-butyl-3-n-propyloxaziridin" *Org. Lett.*(1999) 1(2):281-284.

Asensio, G., et al., "Regioselective Oxyfunctionalization of Unactivated Tertiary and Secondary C—H Bonds of Alkylamines by Methyl(trifluoromethyl)dioxirane in Acid Medium" *J. Am. Chem. Soc.*(1993) 115:7250-7253.

Bioreversible Carriers in Drug Design: Theory and Application 13-21 and Table of Contents (E. B. Roche ed., Pergamon Press New York 1987).

Cao K. et al., "Carbon-14 labeling of Saxagliptin (BMS-477118)" *J Label Compd Radiopharm*(2007) 50:1224-1229.

Contreras, R.H. et al., "Experimental and DFT studies on the transmission mechanisms of analogous NMR $J_{ch}$ and $J_{cc}$ couplings in 1-X- and 1-X-3-methylbicyclo[1.1.1]-pentanes" *Magn. Reson. Chem.*(2007) 45:572-577.

Dasgupta A., et al., "Interaction of White and Pink Grapefruit Juice with Acetaminophen (Paracetamol) In Vivo in Mice" *J. Med. Food*(2008) 11(4):795-798.

Design of Prodrugs (Hans Bundgaard ed., Elsevier 1985) Table of Contents only.

Janecki, T., et al., "[n]Staffanes with Terminal Nitrile and Isonitrile Functionalities and their Metal Complexes" *Collect. Czech. Chem. Commun.*(1993) 83:89-104.

Jasys, V. J., et al., "Preparation of Fluoroadamantane Acids and Amines: Impact of Bridgehead Fluorine Substitution on the Solution- and Solid-State Properties of Functionalized Adamantanes" *J. Am. Chem. Soc.*(2000) 122:466-473.

Khusnutdinov, R. I., et al., "Selective Hydroxylation of Adamantane and Its Derivatives" *Russian Journal of Organic Chemistry*(2009) 45(8):1137-1142.

Komiya, N., et al., "Ruthenium-catalysed oxidation of alkanes with peracetic acid in trifluoroacetic acid: ruthenium as an efficient catalyst for the oxidation of unactivated C—H bonds" *Chem. Commun.*(2001):65-66.

Lee, S. et al "Chemospecific Chromium[VI] Catalyzed Oxidation of C—H Bonds at 40° C." *J. Am. Chem. Soc.*(2002) 124:13978-13979.

Linz, T., et al., "Oxidation of Non-Activated C—H Bonds in Hydrocarbons and Steroids" *Tetrahedron Letters*(1987) 28(52):6581-6582.

McNeill, E. et al., "Ruthenium-Catalyzed Hydroxylation of Unactivated Tertiary C—H Bonds" *J. Am. Chem. Soc.*(2010) 132:10202-10204.

McNeill, E. et al., "Catalytic C—H oxidation by a triazamacrocyclic ruthenium complex" *Chem. Sci.*(2012) 3:1810-1813.

Onomura, O., et al., "Efficient Oxidation of Adamantanes by Sodium Nitrite with Molecular Oxygen in Trifluoroacetic Acid" *Synlett,*(2006) 15:2415-2418.

Pätzel, M., et al., "3-Aminobicyclo[1.1.1]pentane-1-carboxylic Acid Derivatives: Synthesis and Incorporation into Peptides" *Eur. J. Org. Chem.*(2004):493-498.

Pritz, S., et al., "Synthesis of a chiral amino acid with bicycle[1.1.1]pentane moiety and its incorporation into linear and cyclic antimicrobial peptides" *Org. Biomed. Chem.*(2007) 5:1789-1794.

Pro-drugs as Novel Delivery Systems (T. Higuchi and V. Stella eds., vol. 14 A.C.S. Symposium Series, American Chemical Society 1975) Table of Contents and Forward only.

Shmailov, A., et al., "Synthesis of functionalized 5-(3-R-1-admantyl)uracils and related compounds" *Tetrahedron*(2010) 66:3058-3064.

Shmailov, A., et al., "First synthesis of α-(3-R-1-adamantyl)sulfoacetic acids and their derivatives" *Tetrahedron*(2012) 68:4765-4772.

Siegers, C.P., "Relations between Hepatotoxicity and Pharmacokinetics of Paracetamol in Rats and Mice" *Pharmacology*(1978) 16:273-278.

Sorochinsky A. E., et al., "Regioselective Oxyfunctionalization of Bridgehead Adamantane Derivatives" *Tetrahedron*(1997) 53(7):5995-6000.

Stepan, A., et al., "Application of the Bicyclo[1.1.1]pentane Motif a Nonclassical Phenyl Ring Bioisostere in the Design of a Potent and Orally Active γ-Secretase Inhibitor" *J. Med. Chem.*(2012) 55: 3414-3424.

Tanemura, K., et al., "Formation of adamantan-1-ols by the reactions of adamantanes with 2,3-dichloro-5,6-dicyano-p-benzoquinone (DDQ) in trifluoromethanesulfonic acid" *J. Chem. Soc., Perkin Trans.*1 ( 2001) 1: 3230-3231.

Wanka, L., et al., "γ-Aminoadamantanecarboxylic Acids Through Direct C—H Bond Amidations" *Eur. J. Org. Chem.*(2007) 2007(9):1474-1490.

Zarubaev V. V. et al., "Synthesis of anti-viral activity of azolo-admantanes against influenza A virus" *Bioorganic& Medicinal Chemistry*(2010) 18:839-848.

International Search Report and Written Opinion dated May 19, 2014 for PCT Application No. PCT/US2014/021038, filed Mar. 6, 2014.

International Preliminary Report on Patentability dated Feb. 24, 2015 for PCT Application No. PCT/US2014/021038, filed Mar. 6, 2014.

Toops et al., "Efficient Synthesis of 1-(Trialkylstannyl)- and 1-(Triarylstannyl)bicyclo[1.1.1]pentanes" *J. Org. Chem.*(1993) 58:6505-6508.

Office Action dated Sep. 17, 2015 for U.S. Appl. No. 14/199,567, filed Mar. 6, 2014.

Adcock et al., "Polar Substituent Effects in the Bicyclo[1.1.1]pentane Ring System: Acidities of 3-Substituted Bicyclo[1.1.1]pentane-1-carboxylic Acids" J.Org. Chem. (2005) 70(3):1029-1034.

Zehnder et al., "Optimization of Potent, Selective, and Orally Bioavailable Pyrrolodinopyrimidine-Containing Inhibitors of Heat Shock Protein 90. Identification of Development Candidate 2-Amino-4{4-chloro-2-[2-(4-fluoro-1*H*-pyrazol-1-yl)ethoxy]-6-methylphenyl}-*N*-(2,2-difluoropropyl)-5,7-dihydro-6*H*-pyrrolo[3,4-d]pyrimidine-6-carboxamide" J. Med. Chem. (2011) 54:3368-3385.

Office Action dated Jan. 20, 2016 for U.S. Appl. No. 14/199,657, filed Mar. 6, 2014.

* cited by examiner

BICYCLIC ANALGESIC COMPOUNDS

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57, such as U.S. Application No. 61/781,580, filed Mar. 14, 2013.

BACKGROUND

1. Field

Described herein are small molecule drugs typified by a bicyclic aliphatic group. The disclosed compounds include analgesic compounds and antipyretic compounds. Also disclosed are methods of synthesis, drug combinations, and medical uses.

2. Description

Nonsteroidal anti-inflammatory compounds, or NSAIDs, are an extremely useful group of small molecule drugs, typified by acetylsalicylic acid, ibuprofen, and naproxen. These are often sold without prescription, and are variously used to treat pain, inflammation, and fever. However, NSAIDs can have undesirable side effects, including gastric upset and/or gastric bleeding.

Acetaminophen, also known as paracetamol or APAP, is also an effective pain reliever often sold over the counter (without prescription). Although it shares analgesic and antipyretic properties with NSAIDs, it has only weak anti-inflammatory properties, and is thus not an NSAID. Unlike many NSAIDs, acetaminophen does not cause gastric upset or bleeding in prescribed doses. Thus, it is an extremely useful drug for those wishing analgesia without adverse gastric side effects.

Acetaminophen is often combined with other drugs for relief of symptoms of influenza and the common cold, among other indications. It is particularly useful in combination with opioid analgesics, where it exhibits synergistic analgesic properties and allows patients to achieve adequate pain relief with lower doses of opioids. The most widely prescribed drug in the United States is a combination of acetaminophen and hydrocodone, with over 130 million prescriptions in the year 2010. Other acetaminophen-opioid combinations, including combinations with oxycodone, are also widely prescribed.

Acetaminophen poisoning is the most common cause of acute liver failure in the Western world, and acetaminophen accounts for the most drug overdoses in the English-speaking world. Acetaminophen is metabolized to form N-acetyl-p-benzoquinoneimine (NAPQI), which depletes glutathione in the liver and injures hepatocytes, leading to acute liver failure and often death. The acetaminophen-opioid combination drugs are commonly implicated in such toxicity, for various reasons. First, patients might not recognize that the prescribed pain relievers contain acetaminophen, and may supplement with acetaminophen if pain relief is inadequate. Second, continued administration of opioids can lead to tolerance and the need for increased dosages to obtain a comparable opioid effect, and users or abusers of the combination drugs may exceed safe dosages of acetaminophen as a consequence.

This has led the U.S. FDA to seek reduced amounts of acetaminophen in the opioid combination drugs and has also led an FDA advisory panel to recommend banning such drugs all together. Although the acetaminophen-opioid drugs remain on the market, there is a strong need for a less toxic replacement without the same hepatotoxicity risks.

Acetaminophen has the structure:

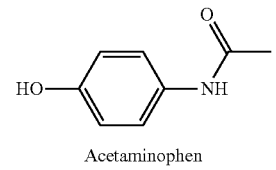

Acetaminophen

Acetaminophen is metabolized in vivo to form the hepatotoxic compound N-acetyl-p-benzoquinoneimine (NAPQI):

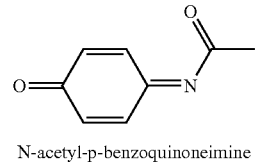

N-acetyl-p-benzoquinoneimine

SUMMARY

Figure 1:
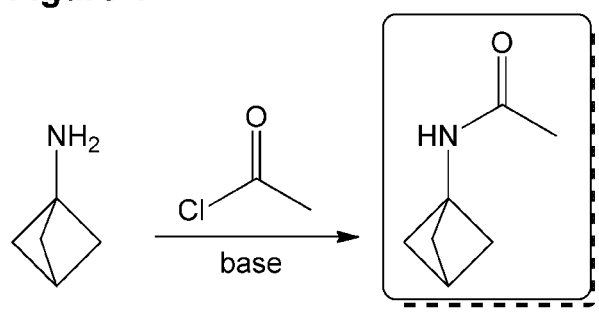
FIG. 1 illustrates a synthetic pathway for creating a bicyclo[1.1.1]pentyl amide compound.

Disclosed herein are compounds having analgesic properties that do not form benzoquinoneimine metabolites and, thus, avoid the hepatotoxicity mechanism of acetaminophen. In some embodiments, the compound having analgesic properties can be a compound of Formula (I), or a pharmaceutically acceptable salt thereof.

Definitions

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from $C_{1-4}$ alkyl (except when the group being substituted is an alkyl, an alkenyl and/or an alkynyl), hydroxy, $C_{1-4}$ alkoxy, cyano, halogen, nitro, halo-$C_{1-4}$ alkyl, halo-$C_{1-4}$ alkoxy and $NH_2$.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, propyl, butyl, pentyl, hexyl, heptyl, and the like.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

The term "alkoxy" used herein refers to straight or branched chain alkyl radical covalently bonded to the parent molecule through an —O— linkage. Examples of alkoxy groups include, but are not limited to, methoxy, ethoxy, propoxy, iso-propoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems. Examples of "aryl" rings include, but are not limited to, optionally substituted phenyl, naphthalenyl, phenanthrenyl, and anthracenyl.

The term, "heterocycle" or "heterocyclyl" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles. An example of an optional substituent includes, but is not limited to, oxo (=O).

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl, and the like. The term "heterocycle" encompasses heteroaryl fused to a non-aromatic ring system.

The term "heteroatom" used herein refers to, for example, oxygen, sulfur and nitrogen.

The term "amino" used herein refers to a nitrogen radical substituted with hydrogen, alkyl, aryl, or combinations thereof. Examples of amino groups include, but are not limited to, —NH(Methyl), —$NH_2$, —N(Methyl)$_2$, —N(Phenyl)(Methyl), —NH(Phenyl), —N(Ethyl)(Methyl), and the like.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-amido may be substituted or unsubstituted.

The term "aryl(alkyl)" used herein refers to one or more aryl groups appended to an alkyl radical. Examples of aryl(alkyl) groups include, but are not limited to, benzyl, phenethyl, phenpropyl, phenbutyl, and the like.

The term "heteroaryl(alkyl)" used herein refers to one or more heteroaryl groups appended to an alkyl radical. Examples of heteroaryl(alkyl) include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pro-drug ester" refers to derivatives of the compounds disclosed herein formed by the addition of any of several ester-forming groups that are hydrolyzed under physiological conditions. Examples of pro-drug ester groups include, but are not limited to fatty acid esters, pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

The abbreviation ($C_n$) in conjunction with the name of a chemical group (e.g., alkyl) refers to the number of carbon atoms in that group. Thus, the term ($C_1$-$C_5$) alkyl means an alkyl group having 1 to 5 carbon atoms.

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and pro-drug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

As used herein, "pharmaceutically acceptable" refers to a material that is not biologically or otherwise undesirable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

The term, "effective amount," as used herein refers to an amount that results in a desired pharmacological and/or physiological effect in an individual who has or is suspected of having (e.g., based on symptoms and/or an individual's perceptions/feelings) a disease or condition or who displays one or more of its symptoms. An effective amount may completely or partially prevent the occurrence or recurrence of the disease or condition or symptom thereof and/or may be therapeutic in terms of a partial or complete cure for the disease or condition and/or adverse effect attributable to the disease or condition (e.g., pain). In reference to a disease or condition described herein (e.g., pain), an effective amount may comprise an amount sufficient to, among other things, reduce and/or relieve to some extent one or more of the symptoms associated with a disease or condition that is responsive to acetaminophen (e.g., pain, fever, inflammation, ischemic injury (such as myocardial and/or cerebral), or neuronal injury). In certain embodiments, the effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease or condition. Effective amount also includes halting or slowing the progression of the disease or condition, regardless of whether improvement or the disease or condition is realized.

The "effective amount" may vary depending on the composition being administered, the condition being treated/prevented (e.g., the type of pain), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and an acetaminophen prodrug may be considered to be given in an effective amount if, in conjunction with one or more additional pharmaceutical agents, one or more desirable or beneficial result(s) may be or are achieved.

When used with respect to methods of treatment and/or prevention and the use of the compounds of Formula (I), or a pharmaceutically acceptable salt thereof, described herein, an individual "in need thereof" may be an individual who has been diagnosed with, previously treated for, and/or suspected of having the disease or condition to be treated. With respect to prevention, the individual in need thereof may also be an individual who is at risk for a disease or condition (e.g., a family history of the condition, life-style factors indicative of risk for the condition, etc.).

Some embodiment disclosed herein relate to a compounds of Formula (I), or a pharmaceutically acceptable salt thereof:

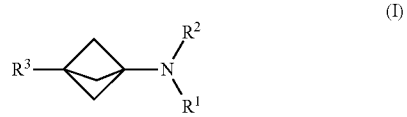

(I)

wherein $R^1$ can be H, —$CH_3$, —$CF_3$, or a substituted or unsubstituted ($C_2$ to $C_5$) alkyl; $R^2$ can be H or —C(=Y)$R^4$; $R^3$ can be H, F, D, hydroxy, $NH_2$, a ($C_1$ to $C_{10}$) alkoxy, a substituted or unsubstituted ($C_1$ to $C_{30}$) alkyl, a substituted or unsubstituted ($C_2$ to $C_{30}$) alkenyl, a substituted or unsubstituted ($C_2$ to $C_{30}$) alkynyl, a substituted or unsubstituted ($C_3$ to $C_{30}$) cycloalkyl, a substituted or unsubstituted ($C_3$ to $C_{30}$) cycloalkenyl, a substituted or unsubstituted ($C_8$ to $C_{30}$) cycloalkynyl, a substituted or unsubstituted ($C_6$ to $C_{30}$) aryl, a substituted or unsubstituted heteroaryl, a substituted or unsubstituted heterocyclyl, a substituted or unsubstituted aryl($C_{1-6}$ alkyl), a substituted or unsubstituted heteroaryl ($C_{1-6}$ alkyl), a substituted or unsubstituted —N-linked amido, —C(=O)L or —O(C=O)$R^5$, wherein —C(=O)L is a hydrolyzable prodrug ester leaving group; $R^4$ can be $CF_3$ or a substituted or unsubstituted ($C_1$ to $C_{10}$) alkyl; $R^5$ can be a substituted or unsubstituted ($C_1$ to $C_6$) alkyl or a substituted or unsubstituted aryl($C_{1-6}$ alkyl); and Y can be S or O; and with the proviso that when $R^3$ hydrogen, then $R^1$ and $R^2$ cannot both be hydrogen.

In some embodiments, $R^1$ can be H (hydrogen). In other embodiments, $R^1$ can be —$CH_3$. In still other embodiments, $R^1$ can be $CF_3$. In some embodiments, $R^1$ can be a substituted ($C_2$ to $C_5$) alkyl. In other embodiments, $R^1$ can be an unsubstituted ($C_2$ to $C_5$) alkyl.

In some embodiments, $R^2$ can be H (hydrogen). In other embodiments, $R^2$ can be C(=O)$R^4$. In still other embodiments, $R^2$ can be C(=S)$R^4$. In some embodiments, both $R^1$ and $R^2$ can be hydrogen. In other embodiments, $R^1$ can be hydrogen, and $R^2$ can be C(=Y)$R^4$.

In some embodiments, $R^3$ can be H. In other embodiments, $R^3$ can be F. In other embodiments, $R^3$ can be D (deuterium). In yet still other embodiments, $R^3$ can be hydroxy. In other embodiments, $R^3$ can be $NH_2$. In other embodiments, $R^3$ can be ($C_1$ to $C_{10}$) alkoxy.

In some embodiments, $R^3$ can be a substituted ($C_1$ to $C_{30}$) alkyl. In other embodiments, $R^3$ can be an unsubstituted ($C_1$ to $C_{30}$) alkyl. In some embodiments, $R^3$ can be a substituted ($C_1$ to $C_6$) alkyl. In other embodiments, $R^3$ can be an unsubstituted ($C_1$ to $C_6$) alkyl, for example, methyl, ethyl, n-propyl, iso-propyl, n-butyl, iso-butyl, tert-butyl, pentyl (straight or branched) or hexyl (straight or branched).

In some embodiments, $R^3$ can be a substituted ($C_2$ to $C_{30}$) alkenyl. In other embodiments, $R^3$ can be an unsubstituted ($C_2$ to $C_{30}$) alkenyl. In some embodiments, $R^3$ can be a substituted ($C_2$ to $C_{30}$) alkynyl. In other embodiments, $R^3$ can be an unsubstituted ($C_2$ to $C_{30}$) alkynyl.

In some embodiments, $R^3$ can be a substituted ($C_3$ to $C_{30}$) cycloalkyl. In some embodiments, $R^3$ can be an unsubstituted ($C_3$ to $C_{30}$) cycloalkyl. In some embodiments, $R^3$ can be a substituted ($C_3$ to $C_{30}$) cycloalkenyl. In some embodiments, $R^3$ can be an unsubstituted ($C_3$ to $C_{30}$) cycloalkenyl. In some embodiments, $R^3$ can be a substituted ($C_6$ to $C_{30}$) cycloalkynyl. In some embodiments, $R^3$ can be an unsubstituted ($C_6$ to $C_{30}$) cycloalkynyl. In some embodiments, $R^3$ can be a substituted or unsubstituted mono-cyclic ($C_3$ to $C_6$) cycloalkyl, a substituted or unsubstituted mono-cyclic ($C_3$ to $C_6$) cycloalkenyl or a substituted or unsubstituted mono-cyclic ($C_8$ to $C_{10}$) cycloalkynyl.

In some embodiments, $R^3$ can be a substituted ($C_6$ to $C_{30}$) aryl. In other embodiments, $R^3$ can be an unsubstituted ($C_6$ to $C_{30}$) aryl. For example, $R^3$ can be a substituted or unsubstituted phenyl or a substituted or unsubstituted naphthyl. When the phenyl is substituted, it can be ortho, meta or para-substituted. The substituted ($C_6$ to $C_{30}$) aryl can be substituted with one or more substituents, and when more than substituents are present, the substituents can be the same or different from each other.

In some embodiments, $R^3$ can be a substituted heteroaryl. In other embodiments, $R^3$ can be an unsubstituted heteroaryl. In some embodiments, $R^3$ can be a substituted or unsubstituted mono-cyclic heteroaryl. In other embodiments, $R^3$ can be a substituted or unsubstituted bi-cyclic heteroaryl.

In some embodiments, $R^3$ can be a substituted heterocycle. In other embodiments, $R^3$ can be an unsubstituted heterocycle. In some embodiments, $R^3$ can be a substituted or unsubstituted mono-cyclic heterocycle. In other embodiments, $R^3$ can be a substituted or unsubstituted bi-cyclic heterocycle.

In some embodiments, $R^3$ can be a substituted aryl($C_{1-6}$ alkyl). In some embodiments, $R^3$ can be an unsubstituted aryl($C_{1-6}$ alkyl). In some embodiments, $R^3$ can be a substituted or unsubstituted benzyl.

In some embodiments, $R^3$ can be a substituted heteroaryl ($C_{1-6}$ alkyl). In some embodiments, $R^3$ can be an unsubstituted heteroaryl($C_{1-6}$ alkyl). In some embodiments, $R^3$ can be a substituted or unsubstituted mono-cyclic heteroaryl ($C_{1-6}$ alkyl). In other embodiments, $R^3$ can be a substituted or unsubstituted bi-cyclic heteroaryl($C_{1-6}$ alkyl).

In some embodiments, $R^3$ can be a substituted heterocyclyl($C_{1-6}$ alkyl). In some embodiments, $R^3$ can be an unsubstituted heterocyclyl($C_{1-6}$ alkyl). In some embodiments, $R^3$ can be a substituted or unsubstituted mono-cyclic heterocyclyl($C_{1-6}$ alkyl). In other embodiments, $R^3$ can be a substituted or unsubstituted bi-cyclic heterocyclyl($C_{1-6}$ alkyl).

In some embodiments, $R^3$ can be —(C=O)L. L can be various groups that together with —C(=O) form a hydrolyzable prodrug ester leaving group. For example, $R^3$ can be —(C=O)O$R^6$, wherein $R^6$ can be a substituted or unsubstituted ($C_1$ to $C_{30}$) alkyl, a substituted or unsubstituted ($C_2$ to $C_{30}$) alkenyl, a substituted or unsubstituted ($C_2$ to $C_{30}$)

alkynyl, a substituted or unsubstituted ($C_3$ to $C_{30}$) cycloalkyl, a substituted or unsubstituted ($C_3$ to $C_{30}$) cycloalkenyl, a substituted or unsubstituted ($C_8$ to $C_{30}$) cycloalkynyl, a substituted or unsubstituted ($C_6$ to $C_{30}$) aryl, a substituted or unsubstituted heteroaryl, a substituted or unsubstituted heterocyclyl, a substituted or unsubstituted aryl($C_{1-6}$ alkyl), a substituted or unsubstituted heteroaryl ($C_{1-6}$ alkyl). In some embodiments, L can be —O—$C_{1-6}$ alkyl. In some embodiments, L can be —$OCH_3$, —$OCH_2CH_3$ or —$OCH_2CH_2OH$.

In some embodiments, $R^3$ can be a substituted or unsubstituted —N-linked amido. For example, $R^3$ can be —NC(=O)—$C_{1-6}$ alkyl. In other embodiments, $R^3$ can be —O(C=O)$R^5$. When $R^3$ is —O(C=O)$R^5$, $R^5$ can be a substituted or unsubstituted ($C_1$ to $C_6$) alkyl or a substituted or unsubstituted aryl($C_{1-6}$ alkyl). In some embodiments, $R^5$ can be a substituted ($C_1$ to $C_6$) alkyl. In other embodiments, $R^5$ can be an unsubstituted ($C_1$ to $C_6$) alkyl. In some embodiments, $R^5$ can be a substituted aryl($C_{1-6}$ alkyl). In other embodiments, $R^5$ can be an unsubstituted aryl($C_{1-6}$ alkyl). A non-limiting list of $R^5$ groups include the following:

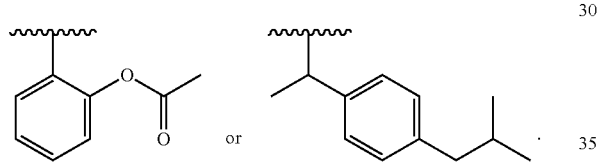

In some embodiments, $R^4$ can be $CF_3$. In other embodiments, $R^4$ can be a substituted ($C_1$ to $C_{10}$) alkyl. In still other embodiments, $R^4$ can be an unsubstituted ($C_1$ to $C_{10}$) alkyl.

Non-limiting examples of compounds of Formula (I) include the following:

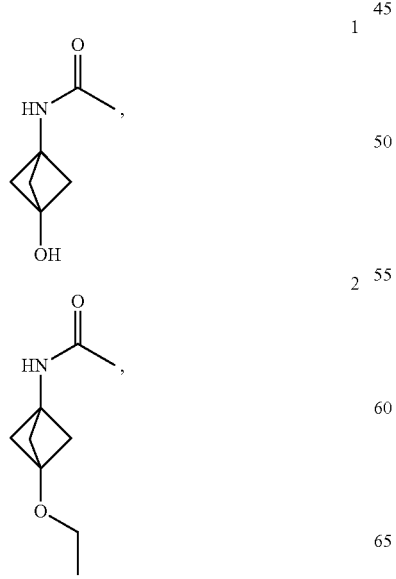

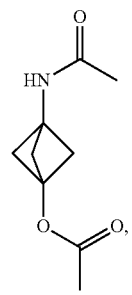

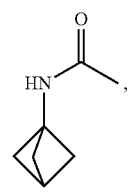

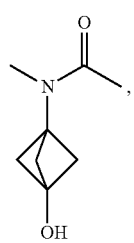

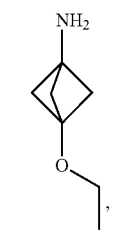

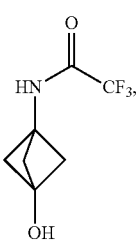

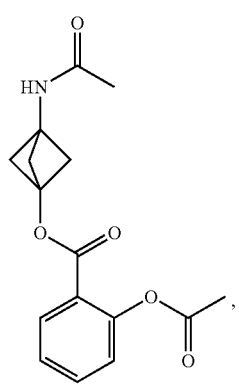

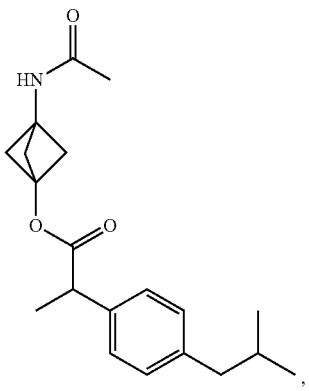

9

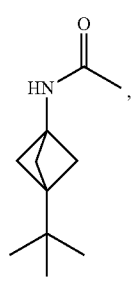

10

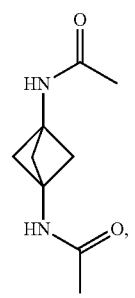

11

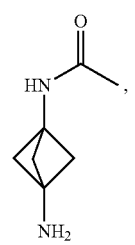

12

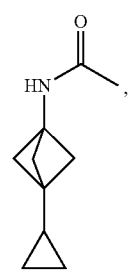

13

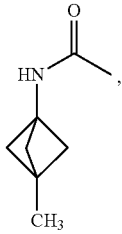

14

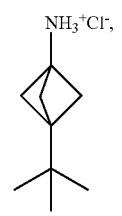

15

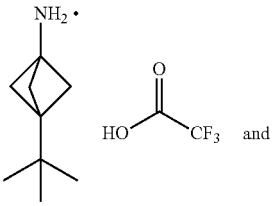

16 and

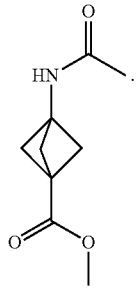

17

As shown herein, compounds of Formula (I), and pharmaceutically acceptable salts thereof, include a core structure having a bicyclo[1.1.1]pentane group. It should be noted that due to valence considerations, it is impossible to connect a substituent through a double bond (such as a carbonyl or imine group) at either end of bicyclo[1.1.1]pentane (i.e., at the 1 or 3 positions). Thus, likely metabolic products of the compounds disclosed herein do not include analogs of benzoquinoneimine, and thus do not present a hepatotoxicity risk through the NAPQI mechanism. In some embodiments, a compound of Formula (I), and pharmaceutically acceptable salts thereof, can have a comparable half-life to acetaminophen. In other embodiments, a compound of Formula (I), and pharmaceutically acceptable salts thereof, can have a longer half-life compared to acetaminophen, for example, about 1.5 times, about 2 times, about 3 times and more than 4 times longer half-life. Thus, a compound of Formula (I), or a pharmaceutically acceptable salt thereof, can be dosed less frequently compared to acetaminophen. For example, a compound of Formula (I), or a pharmaceutically acceptable salt thereof, can be administered every 6 to 8 hours or every 8 to 12 hours or every 24 hours, instead of every 4 to 6 hours as recommended for acetaminophen. Additional advantages of a compound of Formula (I), or a pharmaceutically acceptable salt thereof, can include no determinable inhibition of cytochrome P450's (e.g., 1A2, 2C9, 2C19, 2D6 and/or 3A4), lower plasma binding, liver microsome stability, solubility in aqueous solution and/or stability in human blood and plasma. Methods for determining whether a compound has any of the aforementioned properties are known to those skilled in the art.

Synthesis

Figure 2:
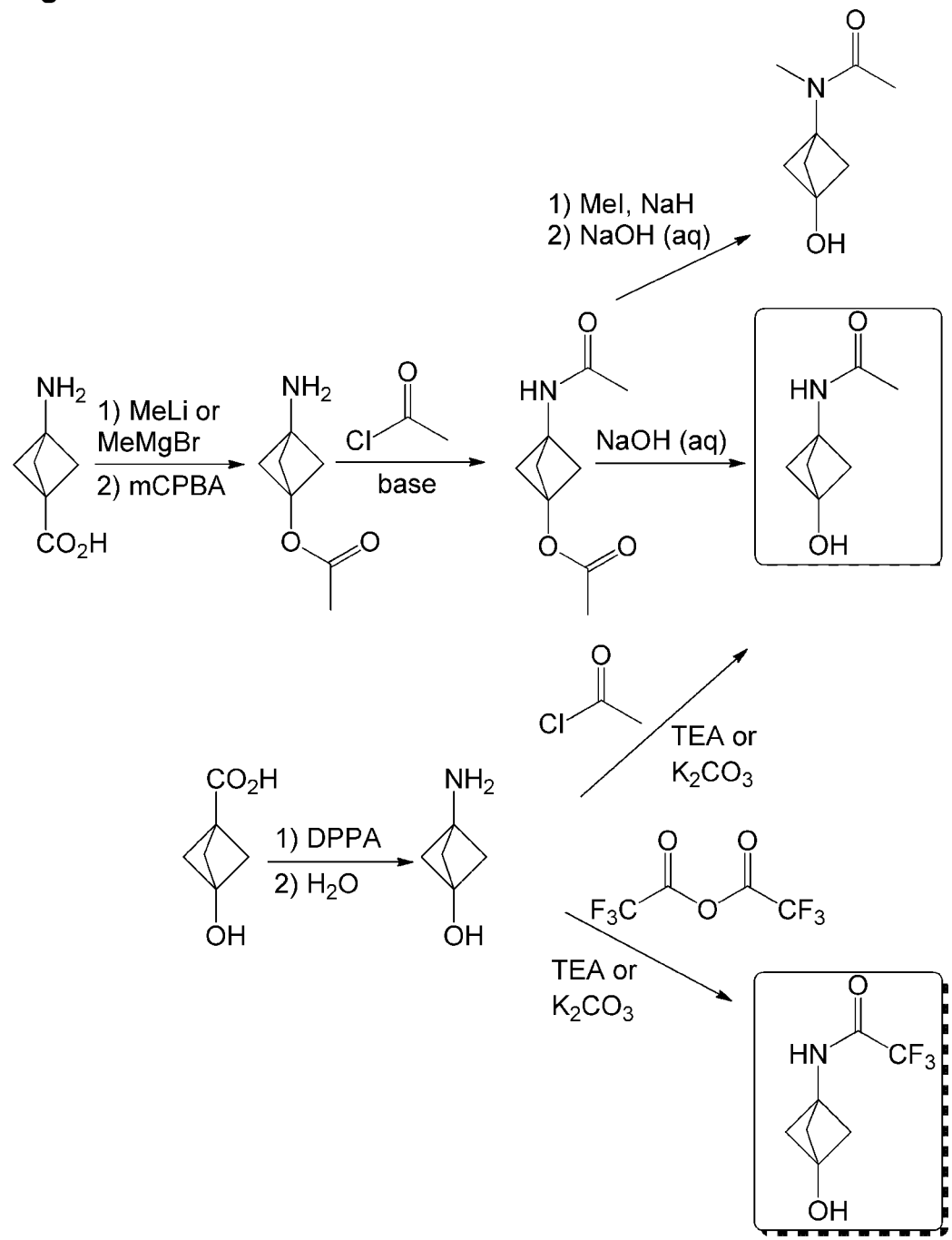
FIG. 2 illustrates a synthetic pathway for creating hydroxy bicyclo[1.1.1]pentyl amide compounds.
Figure 3:
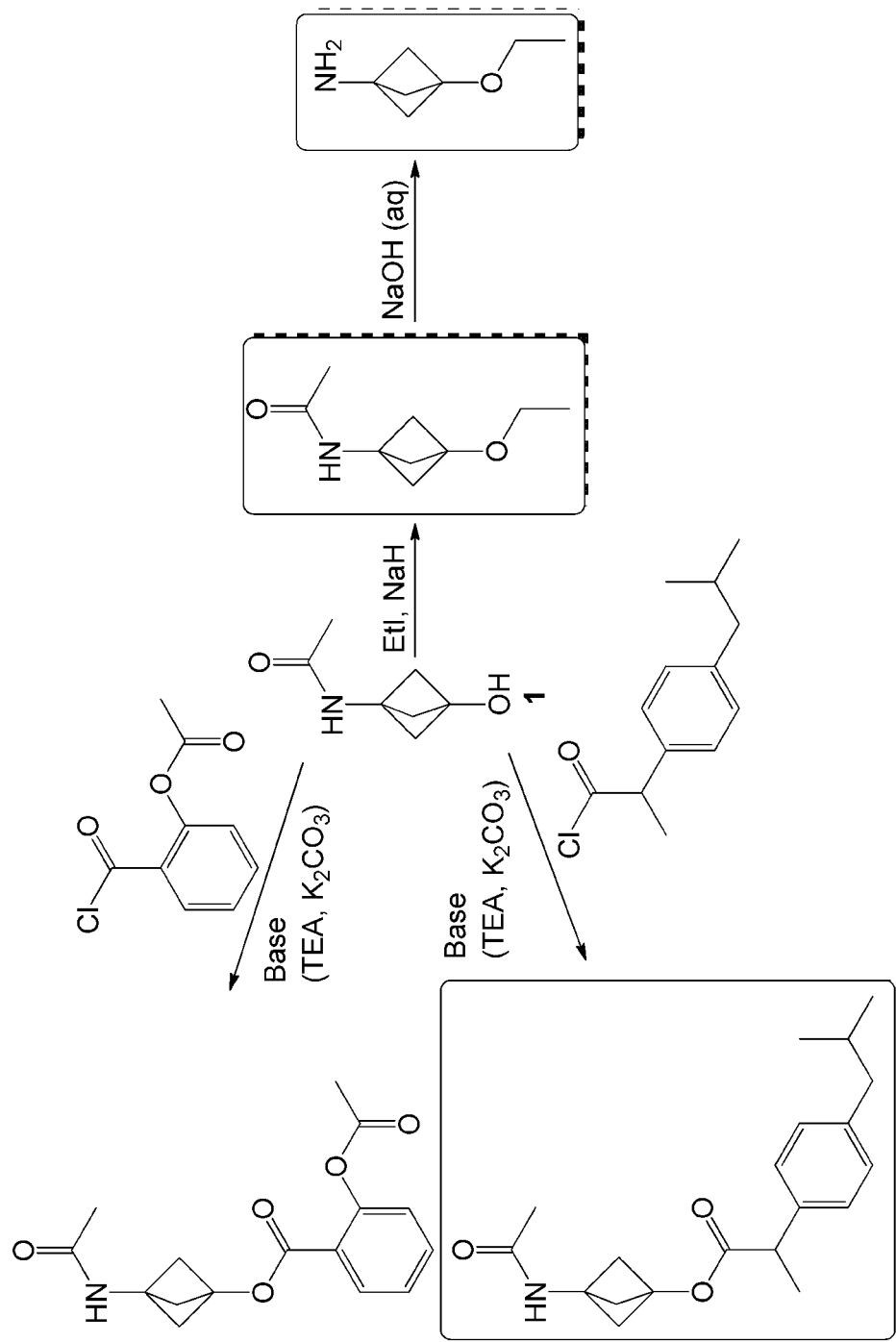
FIG. 3 illustrates a synthetic pathway for creating analgesic ethers and prodrug esters of bicyclo[1.1.1]pentyl compounds.

The various compounds contemplated herein can be synthesized from known starting materials by various routes. Some suitable routes are illustrated in FIGS. 1-3, with syntheses described in more detail in the following description and Schemes.

Scheme 1

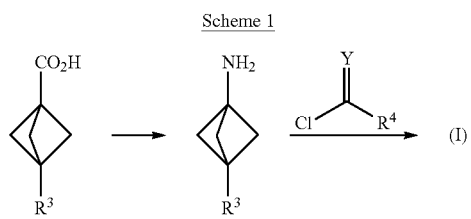

Compounds of Formula (I) can be prepared starting from a compound of Formula (A). The carboxylic acid of the compound of Formula (A) can be transformed to an amino group via a Curtius reaction or modified Curtius reaction. The amino group can then be treated with acetyl chloride to give a compound of Formula (I). Salts can be formed using methods known to those skilled in the art and described herein, for example, reacting an amine with a suitable acid (such as HCl).

or methylmagnesium bromide (Scheme 2). Baeyer-Villager type oxidation with mCPBA or other peroxycarboxylic acids can give 3-aminobicyclo[1.1.1]pentan-1-yl acetate. The amine can then be coupled with an appropriate carboxylic acid or acid chloride, such as acetyl chloride to give 3-acetamidobicyclo[1.1.1]pentan-1-yl acetate (3). Selective hydrolysis of the ester group with hydroxide ion gives N-(3-hydroxybicyclo[1.1.1]pentan-1-yl)acetamide (1). Alternatively, starting with the commercially available 3-hydroxybicyclo[1.1.1]pentane-1-carboxylic acid and carrying out a Curtius reaction or modified Curtius reaction using diphenylphosphoryl azide gives the amino alcohol intermediate, which can then be treated with acetyl chloride (1 eq.) in the presence of base (for example, $K_2CO_3$, $Na_2CO_3$, $NaHCO_3$, TEA, and the like) to give N-(3-hydroxybicyclo[1.1.1]pentan-1-yl)acetamide (1) or with acetyl chloride (>2 eq.) in the presence of base (for example, $K_2CO_3$, $Na_2CO_3$, $NaHCO_3$, TEA, and the like) to give 3-acetamidobicyclo[1.1.1]pentan-1-yl acetate (3).

Scheme 3

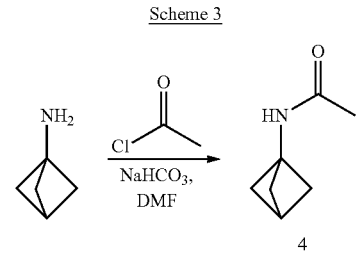

Scheme 2

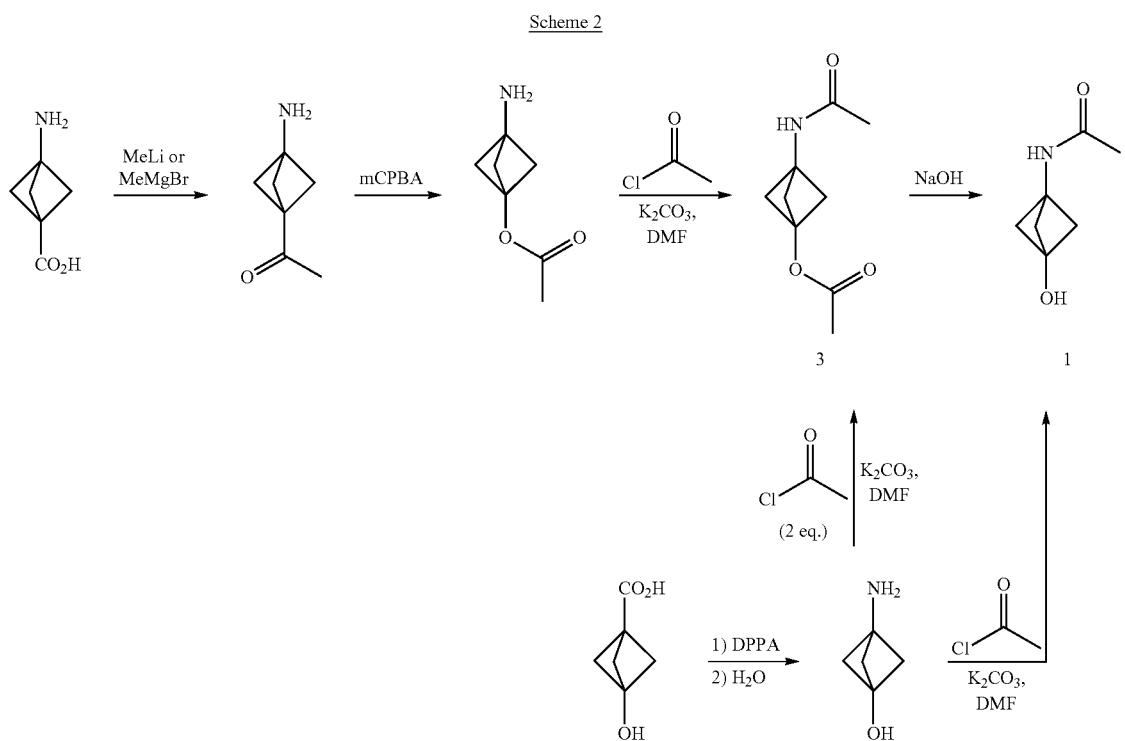

The commercially available 3-aminobicyclo[1.1.1]pentane-1-carboxylic acid can be converted to the methyl ketone intermediate by treatment with either methyl lithium The commercially available bicyclo[1.1.1]pentan-1-amine can be coupled with an appropriate carboxylic acid or acid chloride, such as acetyl chloride in the presence of base (for example, K$_2$CO$_3$, Na$_2$CO$_3$, NaHCO$_3$, TEA, pyridine, and the like) to give N-(bicyclo[1.1.1]pentan-1-yl)acetamide (4) (Scheme 3).

C—H activation or oxidation reagents are described in the following references, which are hereby incorporated by reference in their entirety: H$_2$SO$_4$ (conc.)/HNO$_3$ (conc. or 50%) [Cao K. et al., *J Label Compd Radiopharm* 2007; 50: 1224-1229; Wanka, L., et al., *Eur. J. Org. Chem.* 2007, 1474-1490]; H$_2$SO$_4$ (conc.)/NH$_4$NO$_3$ [Zarubaev V. V. et al., *Bioorganic & Medicinal Chemistry* 18 (2010) 839-848]; perfluoro-cis-2-n-butyl-3-n-propyloxaziridine [Sorochinsky A. E., et al., *Tetrahedron*, 1997, 53, 5995-6000; Amone A., et al., *Org. Lett.*, 1999, 1, 281-284]; CBr$_4$/H$_2$O/Mo(CO)$_6$ [Khusnutdinov, R. I., et al., *Russian Journal of Organic Chemistry*, 2009, 45, 1137-1142]; [(Me$_3$tacn)RuCl$_3$], CAN, AgClO$_4$, t-BuOH/H$_2$On [McNeill, E., Du Bois, J., *Chem. Sci.*, 2012, 3, 1810-1813]; RuCl$_3$-xH$_2$O, KBrO$_3$, H$_2$O, pyridine, CH$_3$CN [McNeill, E., Du Bois, J., *J. Am. Chem. Soc.*, 2010, 132, 10202-10204]; dimethyldioxirane (DMD) or methyl(trifluoromethyl)dioxirane (TFDO), with or without HBF$_4$ [Annese, C., et al., *Org. Lett.*, 2009, 11, 3574-3577; Asensio, G., et al., *J. Am. Chem. Soc.* 1993, 115, 1250-7253]; CrO$_3$, H$_5$IO$_6$ [Lee, S., Fuchs, P. L., *J. Am. Chem. Soc.* 2002, 124, 13978-13979]; KMnO$_4$, KOH [Jasys, V. J., et al., *J. Am. Chem. Soc.*, 2000, 122, 466-473]; H$_2$SO$_4$ (conc.), (CF$_3$CO)$_2$O [Shmailov, A., et al., *Tetrahedron*, 2010, 66, 3058-3064; Shmailov, A., et al., *Tetrahedron*, 2012, 68, 4765-4772]; NaNO$_2$, TFA, O$_2$ [Onomura, O., et al., *Synlett*, 2006, 2415-2418]; CrO$_3$, CH$_3$CO$_2$H, (H$_3$CO)$_2$O [Linz, T., Schäfer, H. J., *Tetrahedron Letters*, 1987, 28, 6581-6582]; RuCl$_3$ (cat.), TFA, DCM, peracetic acid [Komiya, N., et al., *Chem. Commun.*, 2001, 65-66]; DDQ, TfOH [Tanemura, K., et al., *J. Chem. Soc., Perkin Trans.* 1, 2001, 3230-3231].

The C—H activation/oxidation (Scheme 4) of commercially available bicyclo[1.1.1]pentan-1-amine by an appropriate oxidizing reagent or condition (for example, H$_2$SO$_4$ (conc.)/HNO$_3$ (conc. or 50%); H$_2$SO$_4$ (conc.)/NH$_4$NO$_3$; perfluoro-cis-2-n-butyl-3-n-propyloxaziridine; CBr$_4$/H$_2$O/Mo (CO)$_6$; [(Me$_3$tacn)RuCl$_3$], CAN, AgClO$_4$, t-BuOH/H$_2$O; RuCl$_3$-xH$_2$O, KBrO$_3$, H$_2$O, pyridine, CH$_3$CN; dimethyldioxirane (DMD) or methyl(trifluoromethyl)dioxirane (TFDO), with or without HBF$_4$; CrO$_3$, H$_5$IO$_6$; KMnO$_4$, KOH; and the like) can give 3-aminobicyclo[1.1.1]pentan-1-ol. The amino alcohol intermediate can then be coupled with an appropriate carboxylic acid or acid chloride, such as acetyl chloride to give 3-acetamidobicyclo[1.1.1]pentan-1-yl acetate (3). Selective hydrolysis of the ester group with hydroxide ion gives N-(3-hydroxybicyclo[1.1.1]pentan-1-yl)acetamide (1). Alternatively, starting with N-(bicyclo[1.1.1]pentan-1-yl)acetamide (4), C—H activation/oxidation with an appropriate oxidizing reagent or conditions (for example, see listed above, and H$_2$SO$_4$ (conc.), (CF$_3$CO)$_2$O; NaNO$_2$, TFA, O$_2$; CrO$_3$, CH$_3$CO$_2$H, (H$_3$CO)$_2$O; RuCl$_3$ (cat.), TFA, DCM, peracetic acid; DDQ, TfOH; and the like) can give N-(3-hydroxybicyclo[1.1.1]pentan-1-yl)acetamide (1).

Scheme 5

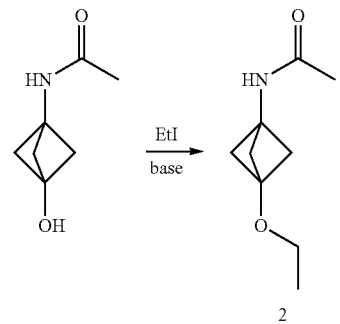

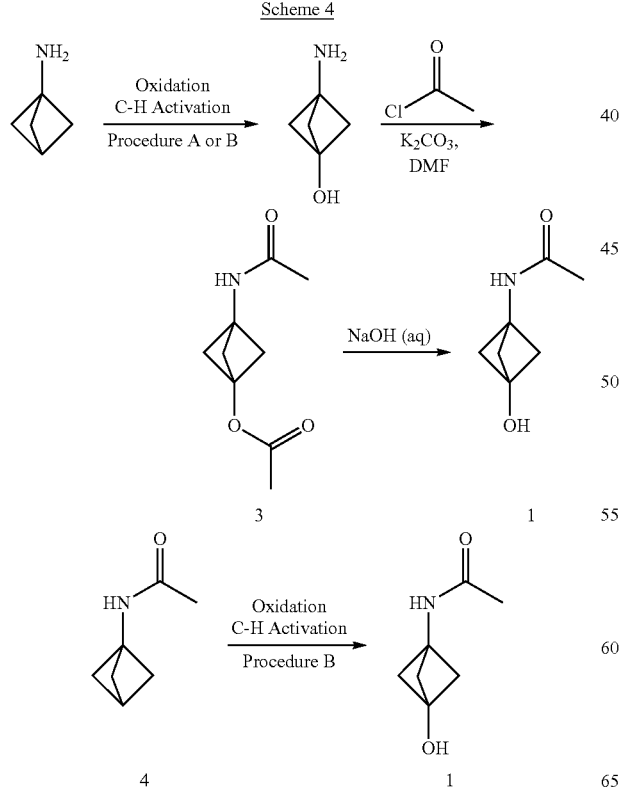

The treatment of N-(3-hydroxybicyclo[1.1.1]pentan-1-yl)acetamide (1) with ethyl iodide in the presence of a base (such as NaHCO$_3$, Na$_2$CO$_3$, TEA, pyridine, NaH, and the like) gives N-(3-ethoxybicyclo[1.1.1]pentan-1-yl)acetamide (2) (Scheme 5).

Scheme 6

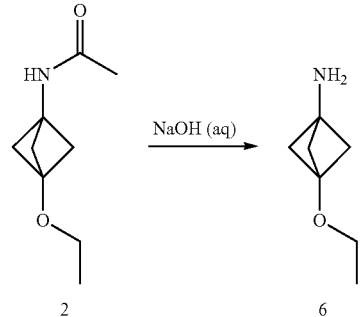

Hydrolysis of N-(3-ethoxybicyclo[1.1.1]pentan-1-yl)acetamide (2) with sodium hydroxide (or basic aqueous conditions) gives 3-ethoxybicyclo[1.1.1]pentan-1-amine (6) (Scheme 6).

Scheme 7

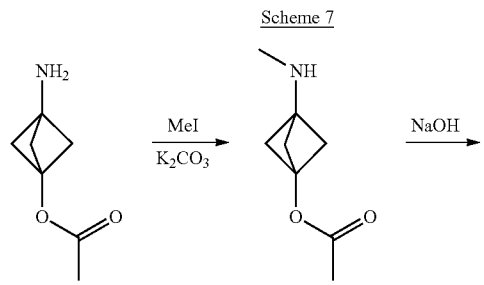

Scheme 8

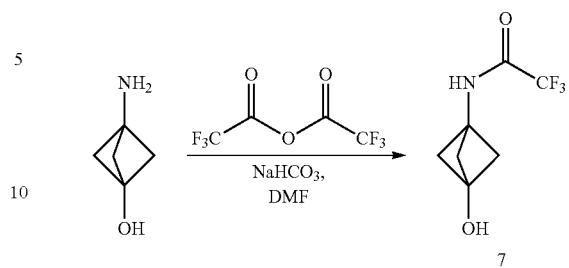

The treatment of 3-aminobicyclo[1.1.1]pentan-1-ol with trifluoroacetic anhydride in the presence of base (for example, $K_2CO_3$, $Na_2CO_3$, $NaHCO_3$, TEA, pyridine, and the like) gives 2,2,2-trifluoro-N-(3-hydroxybicyclo[1.1.1]pentan-1-yl)acetamide (7) (Scheme 8).

Scheme 9

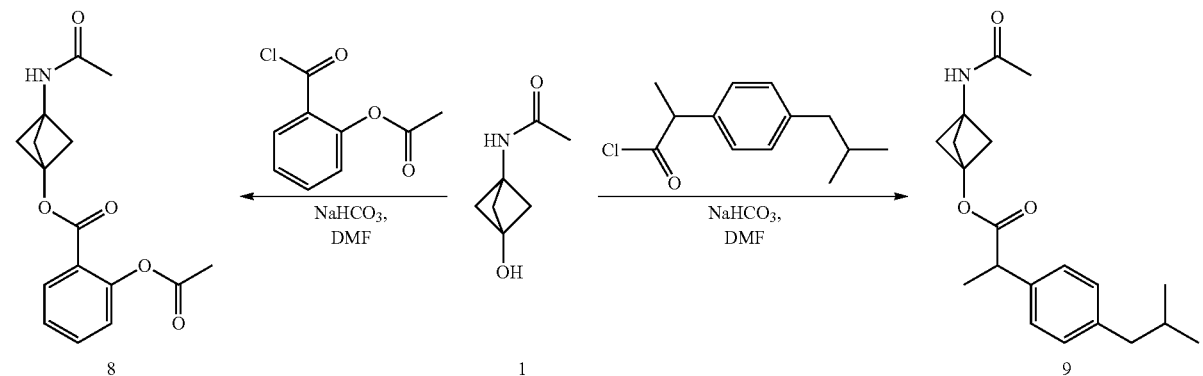

-continued

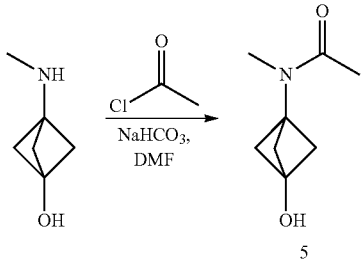

The treatment of 3-aminobicyclo[1.1.1]pentan-1-yl acetate (prepared as depicted in Scheme 2) with methyl iodide in the presence of base leads to 3-(methylamino)bicyclo[1.1.1]pentan-1-yl acetate, followed by hydrolysis with aqueous hydroxide gives 3-(methylamino)bicyclo[1.1.1]pentan-1-ol (Scheme 7). The amino alcohol intermediate can be coupled with an appropriate carboxylic acid or acid chloride, such as acetyl chloride in the presence of base (for example, $K_2CO_3$, $Na_2CO_3$, $NaHCO_3$, TEA, pyridine, NaH, and the like) to give N-(3-hydroxybicyclo[1.1.1]pentan-1-yl)-N-methylacetamide (5).

The treatment of N-(3-hydroxybicyclo[1.1.1]pentan-1-yl)acetamide (1) with O-acetylsalicyloyl chloride in the presence of a base (for example, $K_2CO_3$, $Na_2CO_3$, $NaHCO_3$, TEA, pyridine, and the like) gives 3-acetamidobicyclo[1.1.1]pentan-1-yl 2-acetoxybenzoate (8) (Scheme 9). Alternatively, the coupling of N-(3-hydroxybicyclo[1.1.1]pentan-1-yl)acetamide (1) with O-acetylsalicylic acid in the presence of a coupling agents (for example, HATU, EDCI, HOBt, HOAt, CDI, DCC, $TP_3$, isobutyl chloroformate, and the like) gives 3-acetamidobicyclo[1.1.1]pentan-1-yl 2-acetoxybenzoate (8). Additionally, the treatment of N-(3-hydroxybicyclo[1.1.1]pentan-1-yl)acetamide (1) with 2-(4-isobutylphenyl)propanoyl chloride in the presence of a base (for example, $K_2CO_3$, $Na_2CO_3$, $NaHCO_3$, TEA, pyridine, and the like) gives 3-acetamidobicyclo[1.1.1]pentan-1-yl 2-(4-isobutylphenyl)propanoate (9) (Scheme 9). Alternatively, the coupling of N-(3-hydroxybicyclo[1.1.1]pentan-1-yl)acetamide (1) with (±)-2-(4-isobutylphenyl)propanoic acid in the presence of a coupling agents (for example, HATU, EDCI, HOBt, HOAt, CDI, DCC, $TP_3$, isobutyl chloroformate, and the like) gives 3-acetamidobicyclo[1.1.1]pentan-1-yl 2-(4-isobutylphenyl)propanoate (9).

Formulation and Administration

Some embodiments described herein relates to a pharmaceutical composition, that can include an effective amount of one or more compounds described herein (e.g., a compound of Formula (I)), or a pharmaceutically acceptable salt thereof) and a pharmaceutically acceptable carrier, diluent, excipient or combination thereof. In cases where compounds are sufficiently basic or acidic to form a stable nontoxic acid or base salt, administration of the compound as a salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including but not limited to chloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids (for example, trifluoroacetic acid, acetic acid, succinic acid, lactic acid, malic acid, tartaric acid, citric acid and nicotinic acid) can also be made. Those skilled in the art understand that when a salt is formed, a —$NH_2$ group present on a compound of Formula (I) may become protonated and form a positively charged —$NH_3^+$ group, and the counterion may have a negative charge (for example, $Cl^-$).

In some embodiments, a prodrug of a compound described herein may be administered. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

Compounds of Formula (I), or a pharmaceutically acceptable salt thereof, can be formulated as a pharmaceutical composition and administered to a mammalian host, such as a human patient, in a variety of forms adapted to the chosen route of administration, i.e., orally or parenterally, by intravenous, intramuscular, topical or subcutaneous routes.

Compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 80% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the Compounds of Formula (I) can be determined by comparing their in vitro activity, and in vivo activity in animal models. Such comparison can be done against an established analgesic drug, such as acetaminophen. For example, if a particular compound of Formula (I) is half as active as acetaminophen, then a dosage of approximately twice the established acetaminophen dosage may be appropriate. Conversely, if the compound of Formula (I) is twice as active as acetaminophen, then a dosage of half the established acetaminophen dosage can be used.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will often be in the range of from about 0.15 mg/kg to about 100 mg/kg. For example, a suitable dose will often be in the range from about 1 mg/kg to about 75 mg/kg of body weight per day, such as about 0.75 mg/kg to about 50 mg/kg of body weight of the recipient per day, about 1 mg/kg to about 90 mg/kg of body weight of the recipient per day, or about 10 mg/kg to about 60 mg/kg of body weight of the recipient per day.

The compound is conveniently administered in unit dosage form; for example, containing 1 to 2000 mg, conveniently 10 to 1000 mg, most conveniently, 5 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Methods of Treatment

The compounds of Formula (I) can be used alone or in any of the foregoing combinations with opioids or other drugs to treat a disease or condition (other than inflammation) that is responsive to an NSAID or any condition responsive to acetaminophen (e.g., pain and/or fever). Some embodiments provided herein relate to a method of treating such a disease or condition that can include administering to an individual an effective amount of a compound of Formula (I), or a pharmaceutically acceptable salt thereof. In some embodiments, the individual can be at risk of developing a disease or condition that is responsive to acetaminophen. In some embodiments, the disease or condition can be one or more of the following: pain, fever, inflammation, ischemic injury (such as myocardial and/or cerebral), or neuronal injury. In some embodiments, the individual can be post-operative and has, or is believed to have or has actually developed post-operative pain. In some embodiments, a compound of Formula (I), or a pharmaceutically acceptable salt thereof, can be administered prophylactically, for example, prophylactically for post-operative pain.

Some embodiments generally related to a method of treating pain of any etiology, including acute and chronic pain, and any pain in which acetaminophen analgesic is prescribed. Examples of pain include post-surgical pain; post-operative pain (including dental pain); migraine; headache and trigeminal neuralgia; pain associated with burn, wound or kidney stone; pain associated with trauma (including traumatic head injury); neuropathic pain (e.g., peripheral neuropathy and post-herpetic neuralgia); pain associated with musculo-skeletal disorders; strains; sprains; contusions; fractures; myalgia; rheumatoid arthritis; osteoarthritis; cystitis; pancreatitis; inflammatory bowel disease; ankylosing spondylitis; sero-negative (non-rheumatoid) arthropathies; non-articular rheumatism and peri-articular disorders; and pain associated with cancer (including "break-through pain" and pain associated with terminal cancer). Examples of pain with an inflammatory component (in addition to some of those described above) include rheumatic pain, pain associated with mucositis, and dysmenorrhea. In some embodiments, a method and/or a composition described herein can be used for treating or preventing of post-surgical pain. In some embodiments, a method and/or a composition described herein can be used for treating or preventing of cancer pain. In some embodiments, a method and/or a composition described herein can be used for treating or preventing pain that is selected from pain associated with surgery, trauma, osteoarthritis, rheumatoid arthritis, lower back pain, fibromyalgia, postherpetic neuralgia, diabetic neuropathy, HIV-associated neuropathy and complex regional pain syndrome.

In some embodiments, a compound of Formula (I), or a pharmaceutically acceptable salt thereof, can be used for treating or preventing pain and/or a fever (e.g., in adults, children and/or infants). Compounds of Formula (I), or pharmaceutically acceptable salts thereof, can be used to treat a variety and varying degrees of pain. In some embodiments, the pain can be acute pain (e.g., acute pain following surgery, such as orthopedic surgery of adults, children, and/or infants).

In some embodiments, a compound of Formula (I), or a pharmaceutically acceptable salt thereof, can be used for treating and/or preventing a fever, such as endotoxin-induced fever (e.g., endotoxin-induced fever in adults, children, and/or infants). In some embodiments, the fever can be selected from low-grade fever, moderate fever, high-grade fever and hyperpyrexia fever. In some embodiments, the fever can be selected from Pel-Ebstein fever, continuous fever, intermittent fever, and remittent fever.

As described herein, compounds of Formula (I), or pharmaceutically acceptable salts thereof, can be used to in a various subjects. In some embodiments, the subject can be a child and/or an infant, for example, a child or infant with a fever. In other embodiments, the subject can be an adult.

Some embodiments described herein relate to a method of delaying the onset of analgesia in an individual in need thereof, wherein the method can include administering to the individual an effective amount of a prodrug of Formula (I)

that (in comparison to the parent drug) delays drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours.

Compounds of Formula (I), or a pharmaceutically acceptable salt thereof, can be administered by a variety of methods. In any of the methods described herein, administration can be by injection or infusion, and intravenous administration over the course of 1 minute, 5 minutes, 10 minutes, 30 minutes, 1 hour, 2 hours, 6 hours, 12 hours, 24 hours or longer, or any intermediate time. Such administration can, in some circumstances, substitute for or significantly reduce the need for administration of an opiate, and is of significant benefit in pain management in hospitals or other care facilities. Some methods described herein can include intravenous administration to an individual in need thereof to manage post-operative or other acute or chronic pain, in either a bolus dose or by infusion over minutes, hours, or days.

Other embodiments described herein relate to a method for selecting a therapy for managing or treating pain in an individual in need thereof, that can include evaluating whether the individual is at risk for hepatic toxicity from pain therapy, and selecting therapy with a compound of Formula (I), or a pharmaceutically acceptable salt thereof, to reduce or eliminate such risk. The method can further include administering the selected therapy with a compound of Formula (I), or a pharmaceutically acceptable salt thereof, to the individual.

Combination Drugs

Compounds of Formula (I), or a pharmaceutically acceptable salt thereof, can be administered alone or in combination with another drug(s). In some embodiments, the other drug(s) can be an opioid analgesic. Any of the known opioid analgesics can be combined with a compound of Formula (I), or a pharmaceutically acceptable salt thereof. As non-limiting examples, such opioid analgesics include morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone.

By way of example, an orally available dosage form of a combination of an opioid analgesic with a compound of Formula (I), or a pharmaceutically acceptable salt thereof, may include from about 20 to about 2000 mg of a compound of Formula (I), or a pharmaceutically acceptable salt thereof, in a unit dosage form that also includes one of the following exemplary opioids: 1-20 mg hydrocodone (such as hydrocodone bitartrate), preferably 2.5 mg, 5 mg, 7.5 mg or 10 mg of hydrocodone or salt thereof; or 1-20 mg oxycodone, preferably 2.5 mg, 5 mg, 7.5 mg or 10 mg of hydrocodone or salt thereof (such as the hydrochloride salt).

Other combinations include combination of a compound of Formula (I), or a pharmaceutically acceptable salt thereof, with butalbital, codeine, dihydrocodeine, ibuprofen, aspirin, and/or naproxen. The other drug(s) can be administered using routes known to those skilled in the art and/or described herein. In some embodiments, a compound of Formula (I), or a pharmaceutically acceptable salt thereof, and another drug(s) can be administered in the same dosage form. In other embodiments, a compound of Formula (I), or a pharmaceutically acceptable salt thereof, and another drug(s) can be administered in the separate dosage forms. In some embodiments, a compound of Formula (I), or a pharmaceutically acceptable salt thereof, and another drug(s) can be by the same route (for example, both intravenously) or by different routes (for example, one orally and the other intravenously).

In some embodiments, a combination of a compound of Formula (I), or a pharmaceutically acceptable salt thereof, and an opioid analgesic can synergistically relieve pain. In some embodiments, the synergistic relief of pain can reduce opioid use. Some embodiments disclosed herein relate to a method of managing, treating, and/or reducing pain that can include administering an effective amount of a combination of a compound of Formula (I), or a pharmaceutically acceptable salt thereof, and an opioid analgesic to an individual. Some embodiments disclosed herein relate to a method for reducing opioid use in pain management, that can include administering an amount of a compound of Formula (I), or a pharmaceutically acceptable salt thereof, in combination with an amount of an opioid analgesic, wherein the amount of the opioid analgesic in the combination is less than the amount of opioid analgesic needed to achieve approximately the same level of pain management when the opioid analgesic is administered alone. Methods known for evaluating pain management is known to those skilled in the art, for example, pain assessment tools. Some embodiments disclosed herein relate to a method for decreasing the risk of opioid dependency that can include administering an amount of a compound of Formula (I), or a pharmaceutically acceptable salt thereof, in combination with an amount of an opioid analgesic, wherein the amount of the opioid analgesic in the combination is less than the amount of opioid analgesic needed to achieve approximately the same level of pain management when the opioid analgesic is administered alone. Some embodiments disclosed herein relate to a method for treating pain and/or fever along with treating opioid dependency that can include administering an amount of a compound of Formula (I), or a pharmaceutically acceptable salt thereof, in combination with an amount of an opioid analgesic.

EXAMPLES

The disclosure can be further understood with reference to the following non-limiting Examples, which are not in any way intended to limit the scope of the claims.

Example 1

Preparation of
N-(3-hydroxybicyclo[1.1.1]pentan-1-yl)acetamide
(1)

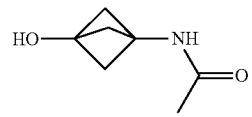

Step 1.

To a solution of 3-aminobicyclo[1.1.1]pentane-1-carboxylic acid (1 mmol) in anhydrous THF (2 mL) at 0° C. under nitrogen is added a methyllithium (1.4 M in diethyl ether, 4 mmol) in a dropwise manner. After addition, the reaction mixture is slowly allowed to warm to room temperature (r.t.), stirred overnight, and treated with aqueous saturated ammonium chloride solution (4 mL). Ethyl acetate (2 mL)

is added and organic layer are separated. The aqueous layer is extracted with ethyl acetate (3×1 mL). The combined organic layers are dried (Mg$_2$SO$_4$) and concentrated. The residue is purified by a flash chromatography on silica gel (EtOAc/hexanes) to give 1-(3-aminobicyclo[1.1.1]pentan-1-yl)ethanone.

Step 2.

A solution of 1-(3-aminobicyclo[1.1.1]pentan-1-yl)ethanone (1 mmol) in 0.5 mL of chloroform is added to a stirred mixture of m-chloroperbenzoic acid (1.5 mmol) in 2 mL of chloroform at r.t. The solution is stirred in the dark for 24 h. The mixture is filtered, and the filtrate is washed with 10% sodium bicarbonate and then water. The organic layer is dried over magnesium sulfate and concentrated. The residue is purified by a flash chromatography on silica gel (EtOAc/hexanes) to give 3-aminobicyclo[1.1.1]pentan-1-yl acetate.

Step 3.

To a DMF (2 mL) solution of 3-aminobicyclo[1.1.1]pentan-1-yl acetate (1 mmol) is added sodium bicarbonate (3 mmol) and then acetyl chloride (1 mmol) by syringe at 0° C. The reaction is allowed to warm up to r.t. and monitored by LCMS. After LCMS analysis indicated consumption of starting material, the reaction is diluted with water and extracted with EtOAc (3×). The organic layers are combined, washed with brine, dried (magnesium sulfate), filtered, and concentrated. The crude residue is subjected to flash chromatography (silica gel, EtOAc/hexanes) to give 3-acetamidobicyclo[1.1.1]pentan-1-yl acetate (3).

Step 4.

To a THF (2 mL) solution of 3-acetamidobicyclo[1.1.1]pentan-1-yl acetate (3) (1 mmol) is added methanol (0.7 mL) followed by a aqueous solution of NaOH (1.4 M, 0.7 mL, 1 eq.) at r.t. The mixture is stirred and monitored by TLC. After complete consumption of the starting material, saturated ammonium chloride is added and the mixture is stirred for 5 min. The volatiles are removed under vacuum and the resultant mixture is extracted with EtOAc (3×). The organic layers are combined, dried (magnesium sulfate), filtered, and concentrated. The crude residue is subjected to flash chromatography (silica gel, EtOAc/hexanes) to give compound 1.

Example 2

Preparation of N-(3-ethoxybicyclo[1.1.1]pentan-1-yl)acetamide (2)

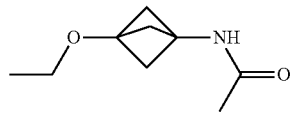

2

To a anhydrous THF (5 mL) solution of N-(3-hydroxybicyclo[1.1.1]pentan-1-yl)acetamide (1) (1 mmol) is added NaH (60% dispersion in mineral oil, 3 mmol) portionwise at 0° C. After addition, the mixture is stirred until the evolution of gas stops. Iodoethane (1 mmol) is then added by syringe slowly. The reaction is monitored by LCMS and TLC. After consumption of starting material, the reaction mixture is quenched by adding water (3 mL) and extracted with ethyl acetate (3×). The organic layers are combined, dried (magnesium sulfate), filtered, and concentrated. The crude residue is subjected to flash chromatography (silica gel, EtOAc/hexanes) to afford compound 2.

Example 3

Preparation of 3-acetamidobicyclo[1.1.1]pentan-1-yl acetate (3)

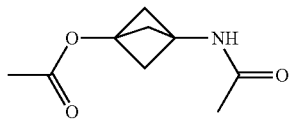

3

The general procedure of Example 1 is repeated to Step 3, to produce 3-acetamidobicyclo[1.1.1]pentan-1-yl acetate (3).

Example 4

Preparation of N-(bicyclo[1.1.1]pentan-1-yl)acetamide (4)

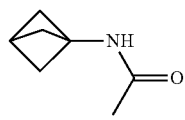

4

To a DMF (12.62 mL) solution of bicyclo[1.1.1]pentan-1-amine, HCl (604 mg, 5.05 mmol) and sodium bicarbonate (1.272 g, 15.14 mmol) was added acetyl chloride (0.359 mL, 5.05 mmol) by syringe at 0° C. The reaction was allowed to warm up to r.t. and monitored by LCMS. After LCMS analysis indicated consumption of starting material, the reaction was diluted with water and extracted with EtOAc (3×). The organic layers were combined, washed with brine and then dried (magnesium sulfate), filtered, and concentrated. The crude residue was subjected to flash chromatography (silica gel, 0-100% EtOAc/hexanes) to give compound 4 as a white solid. MS: m/z 126.2 [M+1]$^+$. $^1$H NMR (CDCl$_3$) ppm: 1.91 (s, 3H), 2.06 (s, 6H), 2.42 (s, 1H), 5.88 (br s, 1H).

Example 5

Preparation of N-(3-hydroxybicyclo[1.1.1]pentan-1-yl)-N-methylacetamide (5)

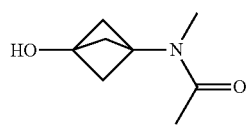

5

Step 1.

To an anhydrous DMF (5 mL) solution of 3-aminobicyclo[1.1.1]pentan-1-yl acetate (1 mmol; prepared as described in Example 1, Step 2) is added potassium carbonate (3 mmol)

followed by the addition of methyl iodide (1 mmol) by syringe at r.t. The reaction is monitored by LCMS and TLC. After consumption of starting material, the reaction mixture is quenched by adding water (3 mL) and extracted with ethyl acetate (3×). The organic layers are combined, dried (magnesium sulfate), filtered, and concentrated. The crude residue is subjected to flash chromatography (silica gel, EtOAc/hexanes) to afford 3-(methylamino)bicyclo[1.1.1]pentan-1-yl acetate.

Step 2.

To a THF (2 mL) solution of 3-acetamidobicyclo[1.1.1]pentan-1-yl acetate (3) (1 mmol) is added methanol (0.7 mL) followed by an aqueous solution of NaOH (4 M, 0.7 mL, 3 eq.) at r.t. The mixture is stirred and monitored by TLC. After complete consumption of the starting material, saturated ammonium chloride (3 mL) is added and the mixture is stirred for 5 min. The volatiles are removed under vacuum and the resultant mixture is extracted with EtOAc (3×). The organic layers are combined, dried (magnesium sulfate), filtered, and concentrated. The crude residue is subjected to flash chromatography (silica gel, EtOAc/hexanes) to give 3-(methylamino)bicyclo[1.1.1]pentan-1-ol.

Step 3.

The general procedure of Example 1 Step 3 is repeated starting with 3-(methylamino)bicyclo[1.1.1]pentan-1-ol to produce compound 5.

Example 6

Preparation of 3-ethoxybicyclo[1.1.1]pentan-1-amine (6)

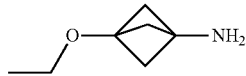

6

The general procedure of Example 5 Step 2 is repeated starting with N-(3-ethoxybicyclo[1.1.1]pentan-1-yl)acetamide (2) to produce compound 6.

Example 7

Preparation of 2,2,2-trifluoro-N-(3-hydroxybicyclo[1.1.1]pentan-1-yl)acetamide (7)

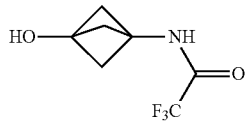

7

The general procedure of Example 1 Step 3 is repeated starting with 3-aminobicyclo[1.1.1]pentan-1-ol and using trifluoroacetic anhydride in place of the acetyl chloride to produce compound 7.

Example 8

Preparation of 3-acetamidobicyclo[1.1.1]pentan-1-yl 2-acetoxybenzoate (8)

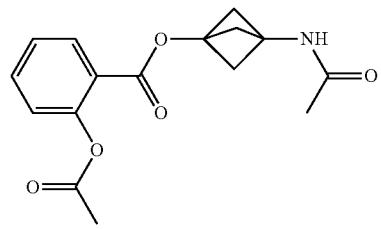

8

The general procedure of Example 1 Step 3 is repeated starting with N-(3-hydroxybicyclo[1.1.1]pentan-1-yl)acetamide (1) and using O-acetylsalicyloyl chloride in place of the acetyl chloride to produce compound 8.

Example 9

Preparation of 3-acetamidobicyclo[1.1.1]pentan-1-yl 2-(4-isobutylphenyl)propanoate (9)

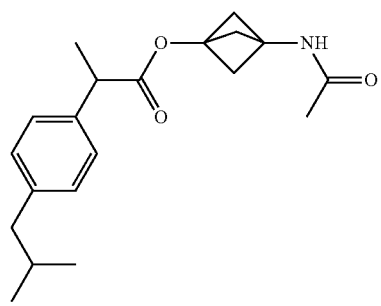

9

The general procedure of Example 1 Step 3 is repeated starting with N-(3-hydroxybicyclo[1.1.1]pentan-1-yl)acetamide (1) and using 2-(4-isobutylphenyl)propanoyl chloride in place of the acetyl chloride to produce compound 9.

Example 10

Preparation of N,N'-(bicyclo[1.1.1]pentane-1,3-diyl)diacetamide (10) and 3-(tert-butyl)bicyclo[1.1.1]pentan-1-amine trifluoroacetate salt (16)

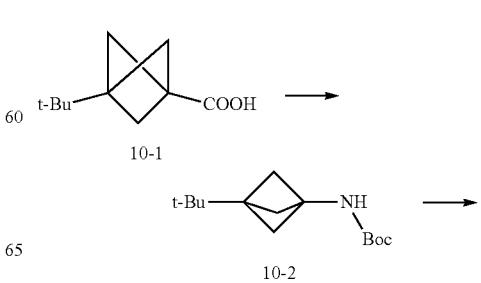

-continued

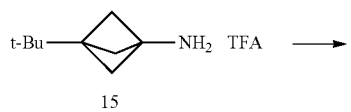

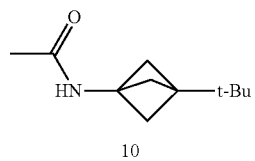

Compound 10-1 was prepared using the procedure provided in Pritz, S., et al., *Org. Biomed. Chem.* 2007, 5, 1789-1794, which is hereby incorporated by reference for the limited purpose of its disclosure of the preparation of compound 10-1. A mixture of 10-1 (1.0 eq.), DPPA (1.2 eq.), Et₃N (2.0 eq.) in dry t-BuOH was stirred at r.t. for 4 h, and then refluxed overnight. The mixture was concentrated, and the residue was extracted with TBME. The solution was washed with brine, dried over MgSO₄, and concentrated. The residue was purified by chromatography (EA:PE=1: 10~1:5) to obtain 10-2 (~30% yield).

A mixture of 10-2 and TFA in DCM was stirred overnight to form compound 16. The solution was concentrated and re-dissolved in DCM. Aqueous NaHCO₃ (pH>8) and AcCl (2.0 eq.) was added at 0° C. and then stirred at r.t. for 30 min. Another portion of aq. NaHCO₃ and AcCl was added. The mixture was extracted with DCM, dried and concentrated. The residue was purified by chromatography (EA:PE=1: 10~1:5) to obtain compound 10 as an off-white solid. (~70% yield). MS: m/z 181.9 [M+1]⁺.

Example 11

Preparation of 3-(tert-butyl)bicyclo[1.1.1]pentan-1-amine chloride salt (15)

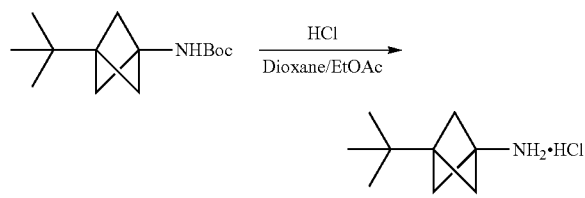

A solution of tert-butyl(3-(tert-butyl)bicyclo[1.1.1]pentan-1-yl)carbamate (0.983 g, 4.11 mmol) in EtOAc (10.3 mL) was treated with HCl (4.0M in dioxane, 41.1 mmol, 10.3 mL) and allowed to stir at r.t. overnight. The solution was concentrated under reduced pressure to afford the crude product as an off-white solid. The solid was triturated with Et₂O (3×10 mL) to afford compound 15 as a white solid (0.6911 g). MS: m/z 140.2 [M+H]⁺.

Example 12

Preparation of N,N'-(bicyclo[1.1.1]pentane-1,3-diyl) diacetamide (11) and N-(3-aminobicyclo[1.1.1]pentan-1-yl)acetamide (12)

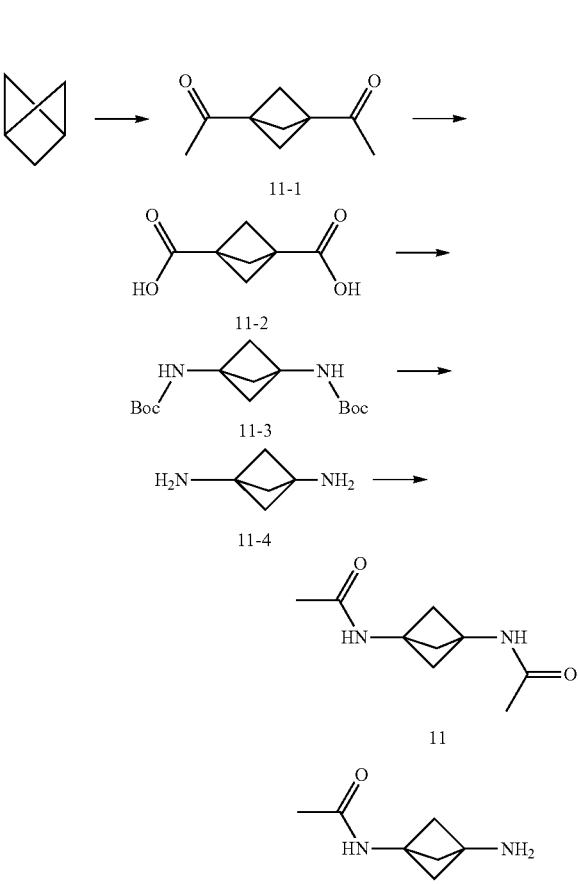

To a solution of [1.1.1]propellane in pentane and ether was added biacetyl (1.2 eq.). The reaction was stirred under the light of a mercury lamp at 0~5° C. for 8 h. The reaction was concentrated to obtain crude 11-1 as a white solid. (50~70% yield).

A solution of 11-1 in dioxane (3 g/10 ml) was added slowly to a solution of NaBrO (prepared by addition of Br₂ (7.6 eq.) to a solution of NaOH (15.6 eq.) in water (~12%) at ~0° C. in water). The mixture was stirred at 0° C. for 1 h, r.t. for 2 h and 50° C. for 1 h. The mixture was extracted using DCM (2 times) and acidified by the addition of conc. HCl. The solution was extracted by ether (over 8 times), dried with MgSO₄ and concentrated to give crude 11-2 as a white solid. The solid was further purified by thoroughly washing with ether to give purified 11-2 (50~80% yield).

The mixture of 11-2 (1.0 eq.), DPPA (2.5 eq.), Et₃N (4.0 eq.) in t-BuOH was stirred at r.t. for 4 h. The solution was refluxed for 24 h, and a suspension formed. The mixture was concentrated and then extracted with TBME. The solution was washed with brine and dried with MgSO₄. The solution was concentrated and purified by chromatography (EA: PE=1:5) to obtain 11-3 as a white solid. (5-30% yield).

To a solution of 11-3 in DCM was added TFA, and the mixture stirred at r.t. for over 2 days. The solution was concentrated to obtain the TFA salt of 11-4. (100% yield).

To a solution of 11-4 in aq. NaHCO₃ (pH>8) at 0° C. was slowly added AcCl (>20 eq.). The reaction was concentrated and extracted with MeOH:DCM (1:10) to obtain a mixture of compounds 11 and 12. The mixture was purified by prep-HPLC to obtain purified compound 11 (~107 mg) and 12. Compound 12 was further purified by reacting compound 12 with CbzCl and aq. NaHCO₃ to give Cbz protected-compound 12. Compound 12 was deprotected using Pd(OH)₂/H₂ in EA:THF, and then purified by prep-HPLC using a TFA system. (~98 mg, 86% yield as TFA salt). Compound 11: MS: m/z 183.1 [M+1]⁺. Compound 12: MS: m/z 141.2 [M+1]⁺.

Example 13

Preparation of methyl 3-acetamidobicyclo[1.1.1]pentane-1-carboxylate (17)

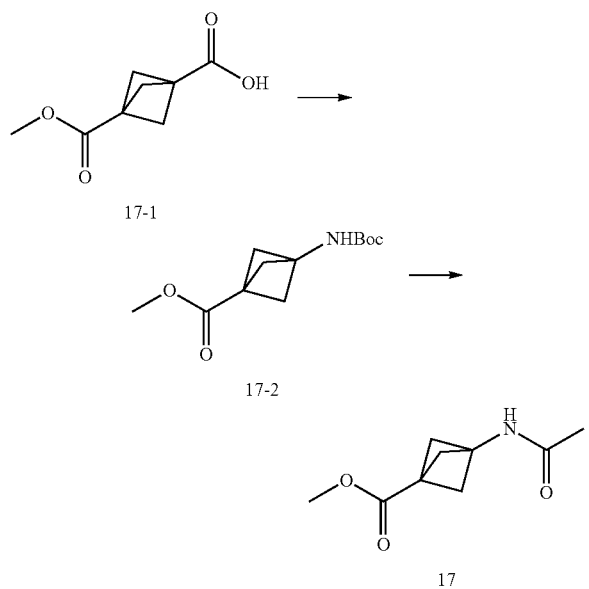

Compound 17-1 was prepared using the procedure provided in Stepan, A., et al., *J. Med. Chem.* 2012 55, 3414-3424, which is hereby incorporated by reference for the limited purpose of its disclosure of the preparation of compound 17-1. A mixture of 17-1, DPPA (1.1 eq.), Et₃N (1.5 eq.) in dry t-BuOH was stirred under N₂ at r.t. for 4 h. The mixture was brought to reflux and maintained for 24 h. The mixture was concentrated, and the residue was extracted using TBME. The solution was washed with brine (3 times). The solution was dried using MgSO₄ and then concentrated to give crude 17-2 as an off-white solid. (~90%) The crude product was purified by chromatography to give purified 17-2 (~50%).

A mixture of 17-2 and TFA in DCM was stirred overnight. The solution was concentrated and re-dissolved in DCM. Aqueous NaHCO₃ (pH>8) and AcCl (2.0 eq.) was added at 0° C. The mixture was stirred at r.t. for 30 min. Another portion of aq. NaHCO₃ and AcCl was added. The reaction was extracted by DCM, dried and concentrated. The residue was purified by chromatography (EA:PE=1:5~1:1) to obtain compound 17 as an off-white solid. (~50% yield). MS: m/z 183.8 [M+1]⁺.

Example 14

Formalin Paw Test

One test compound or the vehicle was administered to each mouse in each test group (8 mice per group). Non-fasted male ICR mice weighing 23±3 g were used. Compounds of Formula (I) were administered at a concentration of 3 mg/kg, 10 mg/kg, 15 mg/kg, 30 mg/kg, 60 mg/kg, 100 mg/kg, 200 mg/kg or 300 mg/kg; morphine was administered at a concentration of 5 mg/kg; and acetaminophen was administered at a concentration of 200 mg/kg. The control group received the vehicle (5% DMSO/40% PEG400/20% HPbCD/Saline). After 30 or 60 minutes, a 2% formalin solution (0.02 mL) was injected into one hind paw (subplantar) of each mouse. Responses were measured every 5 minutes after the formalin injection for 35 minutes.

Figure 4:
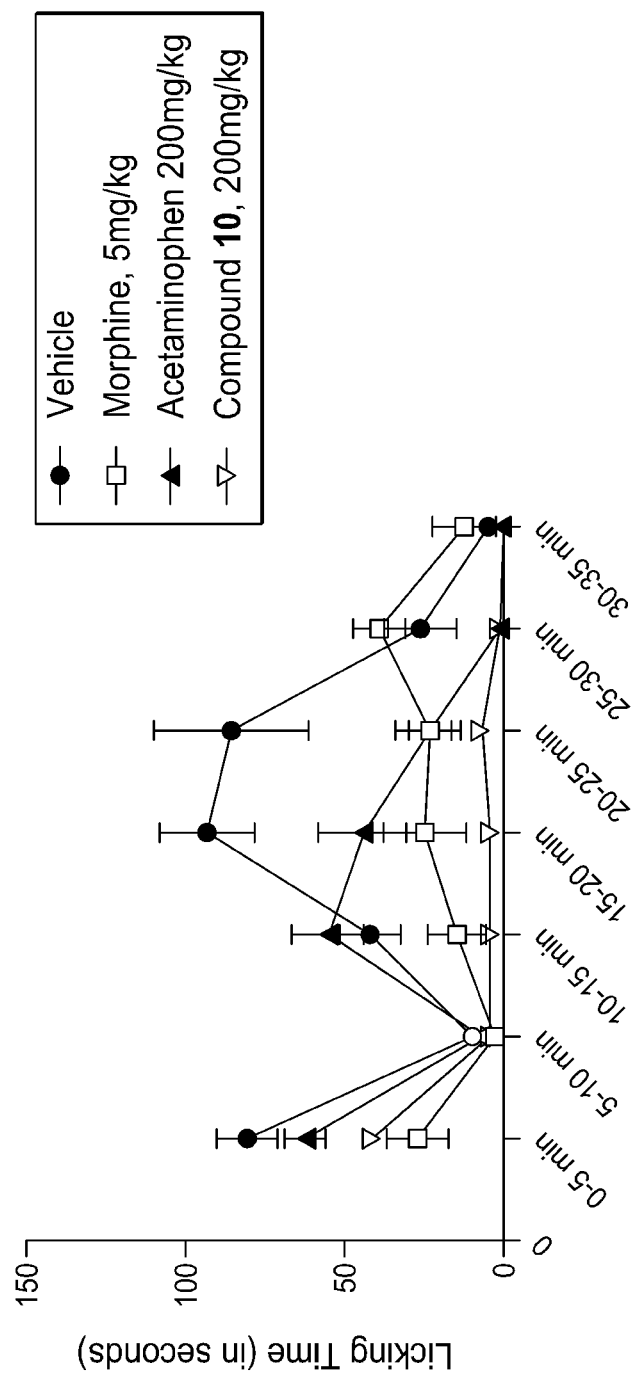
FIG. 4 shows the results from a Formalin Paw Test with the vehicle, morphine, acetaminophen and compound 10.

FIG. 4 shows the results from a Formalin Paw Test with the vehicle, morphine, acetaminophen and compound 10 (200 mg/kg), wherein compound 10 was administered 30 minutes before the formalin injection. As shown in FIG. 4, compound 10 significantly decreased the pain response compared to both acetaminophen and morphine. Additionally, the decrease in pain response lasted through both the early/acute phase (0-5 minutes) and the late/tonic phase (20-35 minutes).

Figure 5:
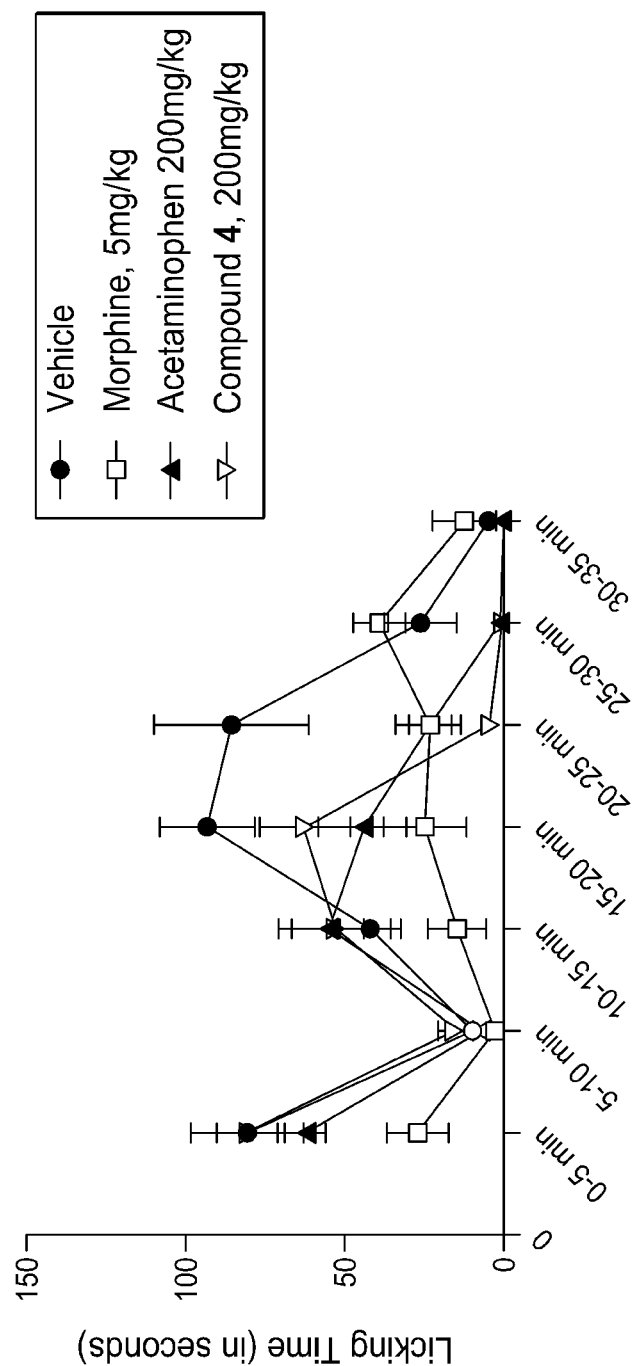
FIG. 5 shows the results from a Formalin Paw Test with the vehicle, morphine, acetaminophen and compound 4.
Figure 10:
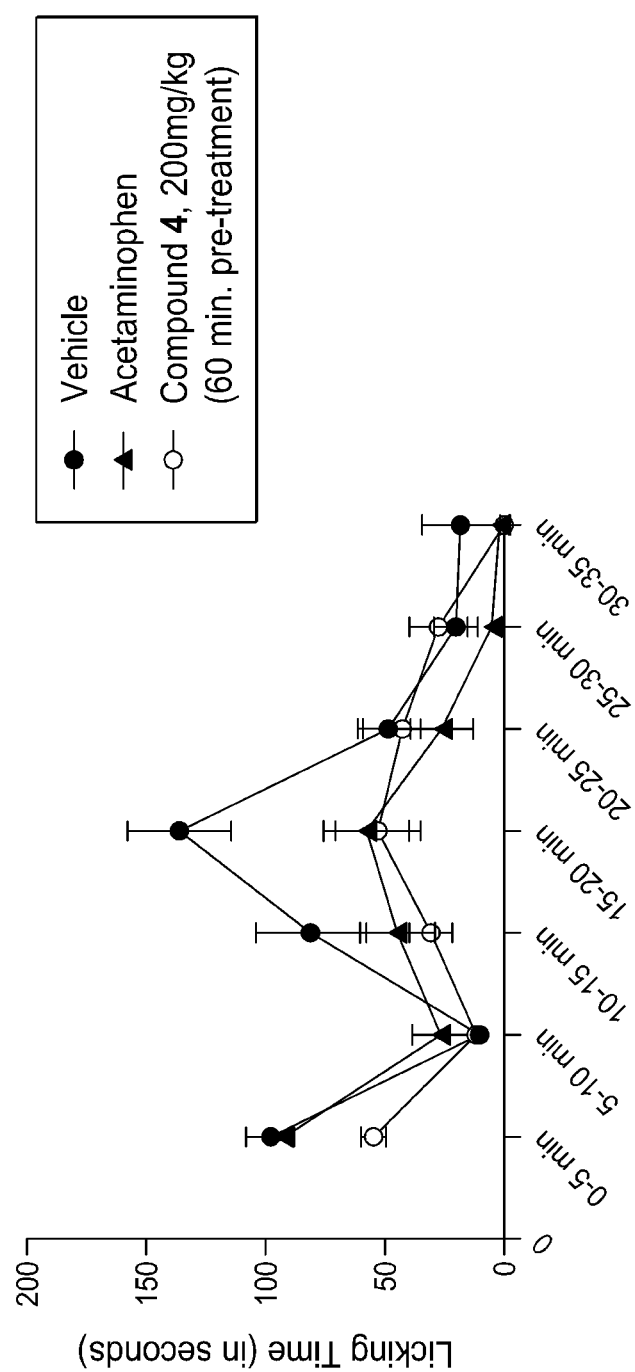
FIG. 10 shows the results from a Formalin Paw Test with the vehicle, acetaminophen and compound 4, in which compound 4 was given 60 minutes before formalin administration.

FIG. 5 shows the results from a Formalin Paw Test with the vehicle, morphine, acetaminophen and compound 4 (200 mg/kg), wherein compound 4 was administered 30 minutes before the formalin injection. FIG. 10 shows the results with compound 4, in which compound 4 was given 60 minutes before formalin administration. As shown in FIG. 5, compound 4 reduces the pain response in a manner similar to acetaminophen for the initial 25 minutes. After 25 minutes, compound 4 demonstrates increased efficacy compared to acetaminophen. When compound 4 was given 60 minutes prior to formalin injection, compound 4 reduces the pain response in a manner similar to acetaminophen throughout the entire testing period. See FIG. 10.

Figure 6:
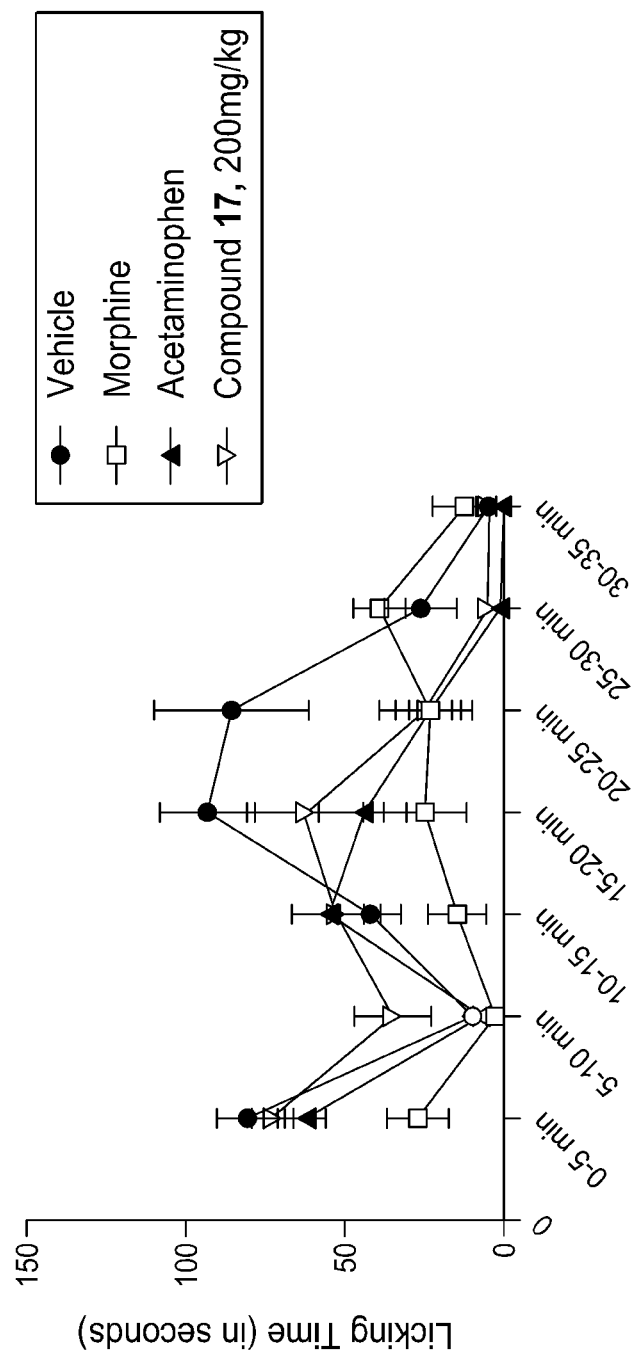
FIG. 6 shows the results from a Formalin Paw Test with the vehicle, morphine, acetaminophen and compound 17.
Figure 7:
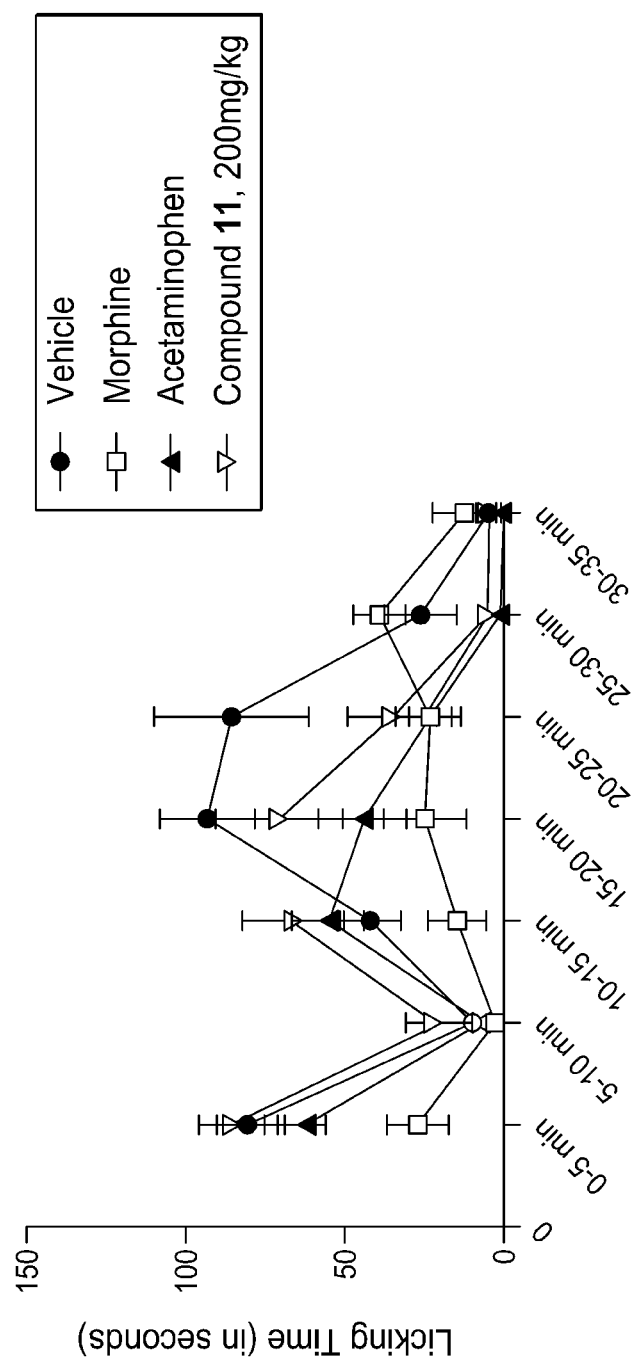
FIG. 7 shows the results from a Formalin Paw Test with the vehicle, morphine, acetaminophen and compound 11.

FIGS. 6 and 7 provide the results from a Formalin Paw Test with the vehicle, morphine, acetaminophen and compound 17 or compound 11, wherein compounds 17 and 11 were give 30 minutes prior to formalin administration. As provided in FIGS. 6 and 7, both compound 17 and 11 demonstrate similar efficacy as acetaminophen.

Figure 8:
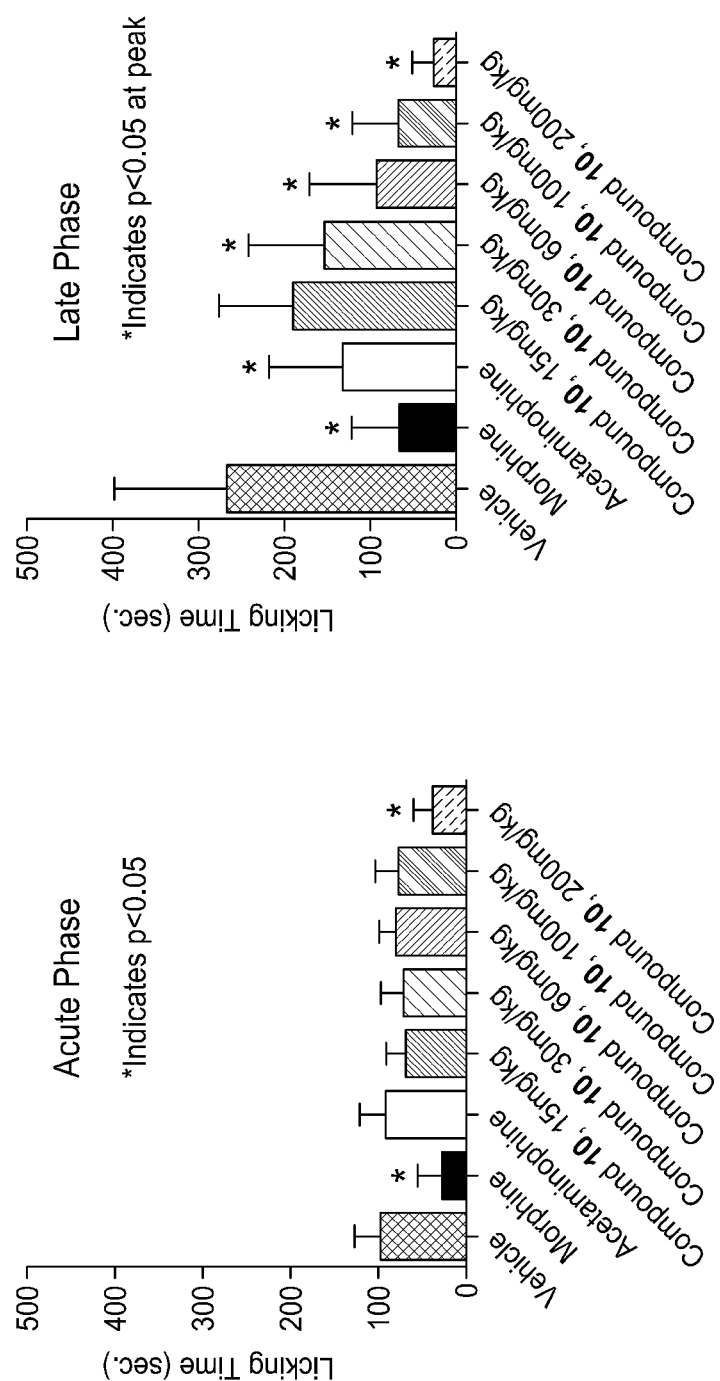
FIG. 8 shows the results from a Formalin Paw Test with different doses of compound 10.
Figure 9:
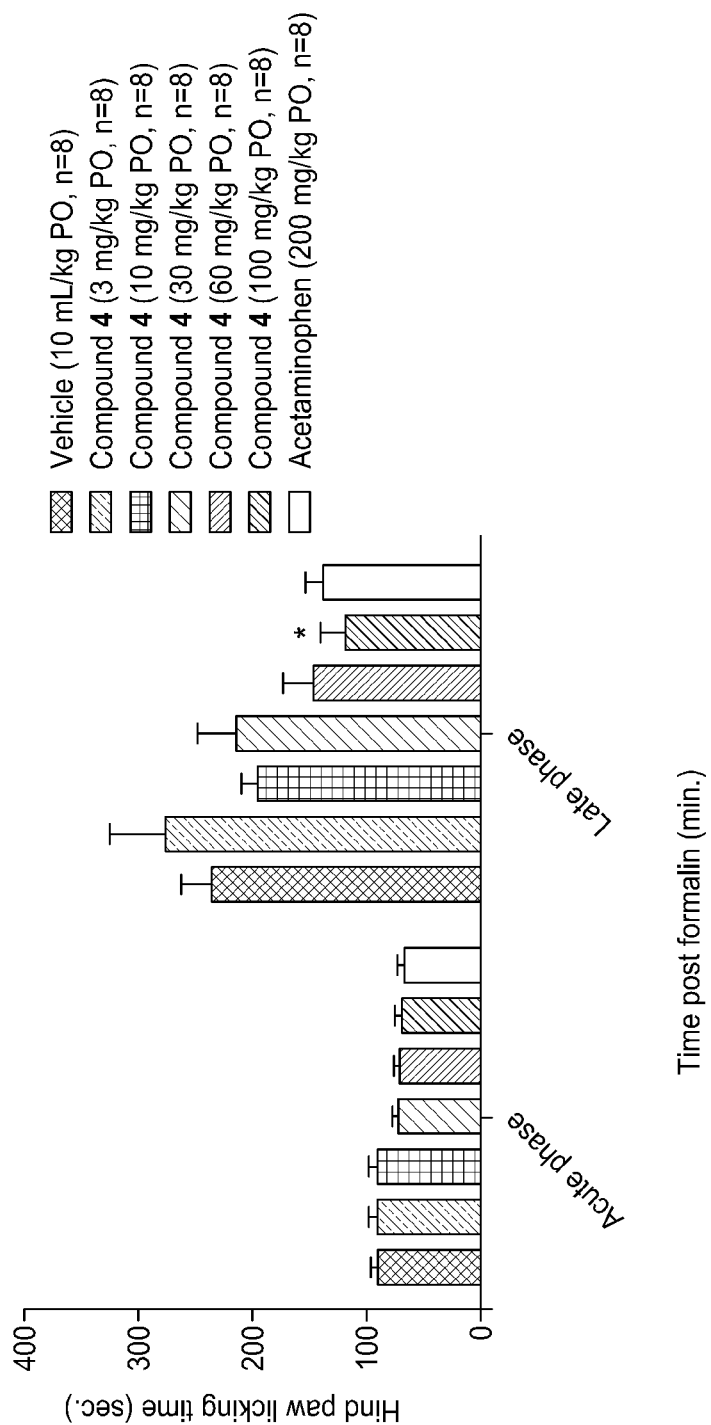
FIG. 9 shows the results from a Formalin Paw Test with different doses of compound 4.

FIGS. 8 and 9 show the results with different doses of compounds 10 and 4, respectively. In the acute phase, compound 10 has equal to or significant increased efficacy compared to acetaminophen at all dosages ranging from 15 mg/kg to 200 mg/kg. See FIG. 8. In the tonic phase, as little as 60 mg/kg of compound 10 was needed to reduce the pain response to a level less than 200 mg/kg of acetaminophen. This amount of compound 10 is about 33% less than the amount of acetaminophen needed to achieve a pain response that is less than acetaminophen. When the dosage of compound 10 was 200 mg/kg, the pain response compared to acetaminophen was approximately 50%.

FIG. 9 shows that the efficacy of compound 4 at dosages ranging from 3 mg/kg to 100 mg/kg. As shown in FIG. 9, a dosage of 60 mg/kg of compound 4 provided a pain response approximately equal to 200 mg/kg of acetaminophen. This amount of compound 4 is about 33% less than the amount of acetaminophen needed to achieve the approximate same pain response.

Example 15

Glutathione Conjugation Assay

An incubation mixture consisting of 5 μL of 10 mM test compound in DMSO (5 μL of DMSO for negative control; 5 μL of 10 mM acetaminophen in DMSO for positive control), 5 μL of 0.1 M glutathione 25 mM EDTA in water, 50 μL of 100 mM MgCl2 in water, 50 μL of 20 mg/mL pooled human liver microsomes (P-450 content: ~0.5 nmol/mg protein), and 340 μL of 100 mM potassium phosphate buffer (pH 7.4) was preincubated at 37° C. for 10 mins. The reaction was initiated by the addition of 50 μL of 100 mM NADPH solution. The final incubation volume was 0.5 mL. The incubation mixture contains 100 μM test compound or acetaminophen (positive control), 1 mM glutathione, and 1 μM P450. After 60 mins incubation at 37° C., 1 mL of chilled acetonitrile was added to stop the reaction. After the addition of acetonitrile, the sample was vortexed and centrifuged. The supernatant was collected, concentrated in TurboVap under N$_2$ (10 psi) at 30° C. for 35 mins, and transferred to a 96-well plate. The plate was capped and centrifuged. The supernatant was injected for LC-MS/MS analysis.

As described herein, acetaminophen can form the reactive metabolite, N-acetyl-p-benzoquinone imine (NAPQI), which is linked to liver toxicity. Acetaminophen is metabolically activated by cytochrome P450 enzymes to form NAPQI, and NAPQI depletes endogenous glutathione (GSH). The depletion of endogenous glutathione leaves cells vulnerable to oxidative damage. The mechanism showing the formation of NAPQI is shown below in Scheme 10. The formation of NAPQI is the result of the phenol ring of acetaminophen.

Scheme 10

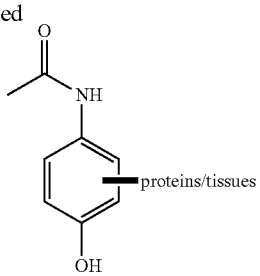

Unlike acetaminophen, compound of Formula (I) do not include a phenol ring and it is impossible to connect a substituent through a double bond (such as a carbonyl or imine group) at either end of bicyclo[1.1.1]pentane (i.e., at the 1 or 3 positions). As a result, one skilled in the art would not expect compounds of Formula (I) to form the reactive metabolite NAPQI. A 129 neutral loss scan can be used to search or detect the formation of glutathione conjugates. Unlike acetaminophen, no glutathione conjugate peak was observed for both compounds 4 and 10; and thus, NAPQI was not formed from compounds 4 and 10.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

In Column 39 at Lines 29-38 (approx.), In Claim 40,
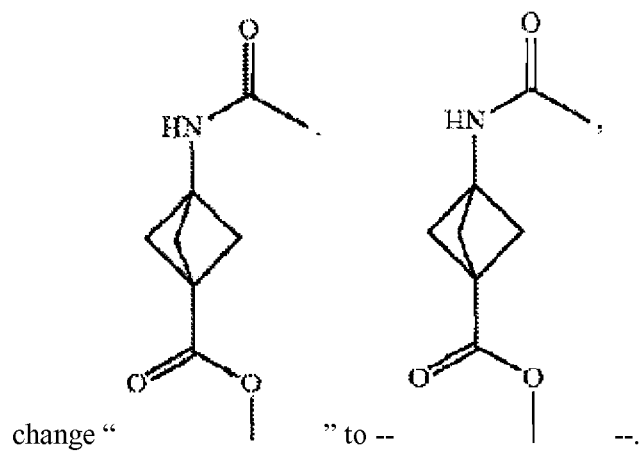

What is claimed is:

1. A method for reducing pain or fever comprising administering an effective amount of a compound of Formula (I), or a pharmaceutically acceptable salt thereof, wherein Formula (I) has the structure:

wherein $R^1$ is H, —CH$_3$, or a substituted or unsubstituted (C$_2$ to C$_5$) alkyl;

$R^2$ is H or —C(=Y)R$^4$;

$R^3$ is H, F, D, hydroxy, NH$_2$, a (C$_1$ to C$_{10}$) alkoxy, a substituted or unsubstituted (C$_1$ to C$_{30}$) alkyl, a substituted or unsubstituted (C$_2$ to C$_{30}$) alkenyl, a substituted or unsubstituted (C$_2$ to C$_{30}$) alkynyl, a substituted or unsubstituted (C$_3$ to C$_{30}$) cycloalkyl, a substituted or unsubstituted (C$_3$ to C$_{30}$) cycloalkenyl, a substituted or unsubstituted (C$_8$ to C$_{30}$) cycloalkynyl, a substituted or unsubstituted —N-linked amido, —(C=O)L or —O(C=O)R$^5$, wherein —(C=O)L is a hydrolyzable prodrug ester leaving group, $R^4$ is a substituted or unsubstituted (C$_1$ to C$_m$) alkyl;

$R^5$ is a substituted or unsubstituted (C$_1$ to C$_6$) alkyl, a substituted or unsubstituted aryl(C$_{1-6}$ alkyl) or

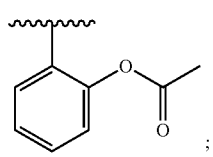

and

Y is S or O.

2. The method of claim 1, further comprising administering an opioid analgesic.

3. The method of claim 2, wherein the opioid analgesic is selected from the group consisting of morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone.

4. The method of claim 1, wherein the administration is intravenous.

5. The method of claim 1, wherein the administration is topical.

6. The method of claim 1, wherein the pain is postoperative pain.

7. The method of claim 1, wherein $R^2$ is —C(=Y)$R^4$.

8. The method of claim 7, wherein Y is O.

9. The method of claim 7, wherein Y is S.

10. The method of claim 1, wherein $R^4$ is a substituted or unsubstituted ($C_1$ to $C_{10}$) alkyl.

11. The method of claim 1, wherein $R^2$ is H.

12. The method of claim 1, wherein $R^1$ is H.

13. The method of claim 1, wherein $R^1$ is —$CH_3$.

14. The method of claim 1, wherein $R^1$ is a substituted or unsubstituted ($C_2$ to $C_5$) alkyl.

15. The method of claim 1, wherein $R^3$ is H.

16. The method of claim 1, wherein $R^3$ is F.

17. The method of claim 1, wherein $R^3$ is D.

18. The method of claim 1, wherein $R^3$ is hydroxy.

19. The method of claim 1, wherein $R^3$ is $NH_2$.

20. The method of claim 1, wherein $R^3$ is a ($C_1$ to $C_{10}$) alkoxy.

21. The method of claim 1, wherein $R^3$ is a substituted or unsubstituted ($C_1$ to $C_{30}$) alkyl.

22. The method of claim 1, wherein $R^3$ is a substituted or unsubstituted ($C_2$ to $C_{30}$) alkenyl.

23. The method of claim 1, wherein $R^3$ is a substituted or unsubstituted ($C_2$ to $C_{30}$) alkynyl.

24. The method of claim 1, wherein $R^3$ is a substituted or unsubstituted ($C_3$ to $C_{30}$) cycloalkyl.

25. The method of claim 1, wherein $R^3$ is a substituted or unsubstituted ($C_3$ to $C_{30}$) cycloalkenyl.

26. The method of claim 1, wherein $R^3$ is a substituted or unsubstituted ($C_8$ to $C_{30}$) cycloalkynyl.

27. The method of claim 1, wherein $R^3$ is a substituted or unsubstituted ($C_6$ to $C_{30}$) aryl.

28. The method of claim 1, wherein $R^3$ is a substituted or unsubstituted heteroaryl.

29. The method of claim 1, wherein $R^3$ is a substituted or unsubstituted heterocyclyl.

30. The method of claim 1, wherein $R^3$ is a substituted or unsubstituted aryl($C_{1-6}$ alkyl).

31. The method of claim 1, wherein $R^3$ is a substituted or unsubstituted heteroaryl($C_{1-6}$ alkyl).

32. The method of claim 1, wherein $R^3$ is a substituted or unsubstituted —N-linked amido.

33. The method of claim 1, wherein $R^3$ is —(C=O)L.

34. The method of claim 33, wherein —(C=O)L is —(C=O)O$R^6$, wherein $R^6$ is a substituted or unsubstituted ($C_1$ to $C_{30}$) alkyl, a substituted or unsubstituted ($C_2$ to $C_{30}$) alkenyl, a substituted or unsubstituted ($C_2$ to $C_{30}$) alkynyl, a substituted or unsubstituted ($C_3$ to $C_{30}$) cycloalkyl, a substituted or unsubstituted ($C_3$ to $C_{30}$) cycloalkenyl, a substituted or unsubstituted ($C_8$ to $C_{30}$) cycloalkynyl, a substituted or unsubstituted ($C_6$ to $C_{30}$) aryl, a substituted or unsubstituted heteroaryl, a substituted or unsubstituted heterocyclyl, a substituted or unsubstituted aryl($C_{1-6}$ alkyl), a substituted or unsubstituted heteroaryl($C_{1-6}$ alkyl).

35. The method of claim 34, wherein $R^3$ is —(C=O)L, and L is —O—$C_{1-6}$ alkyl.

36. The method of claim 1, wherein $R^3$ is —O(C=O)$R^5$.

37. The method of claim 36, wherein $R^5$ is a substituted or unsubstituted ($C_1$ to $C_6$) alkyl.

38. The method of claim 36, wherein $R^5$ is a substituted or unsubstituted aryl($C_{1-6}$ alkyl).

39. The method of claim 36, wherein $R^5$ is

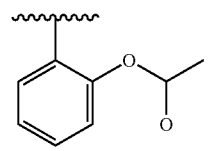

40. The method of claim 1, wherein the compound is selected from the group consisting of:

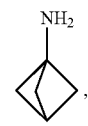

1

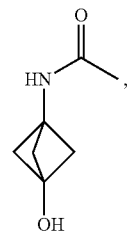

2

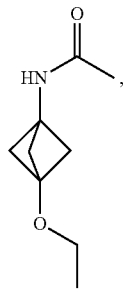

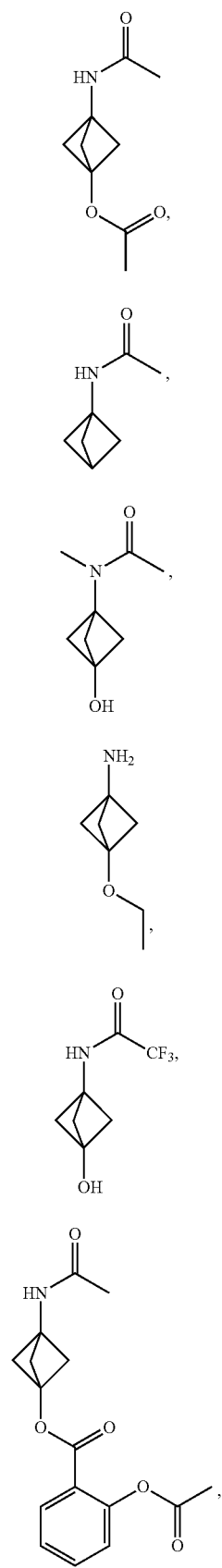
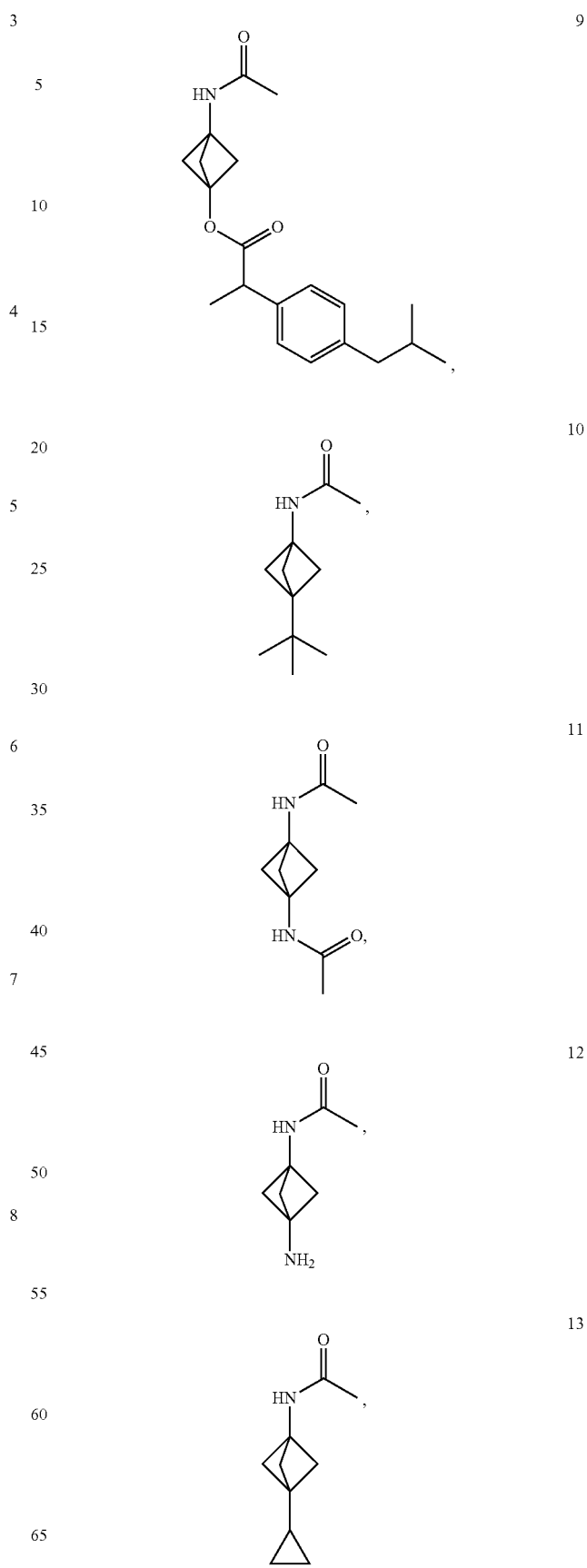

-continued

14

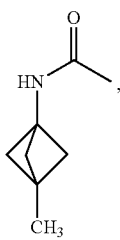

15

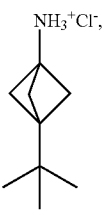

16

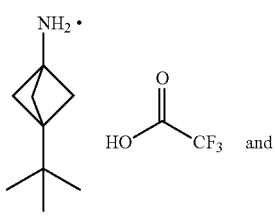

17

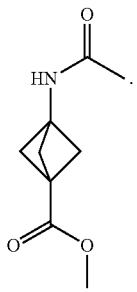

or a pharmaceutically acceptable salt of the foregoing.

41. A compound of Formula (I), or a pharmaceutically acceptable salt thereof:

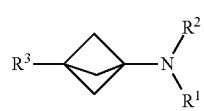 (I)

wherein
$R^1$ is H, —CH$_3$, —CF$_3$, or a substituted or unsubstituted (C$_2$ to C$_5$) alkyl;
$R^2$ is —C(=Y)R$^4$; and
$R^3$ is H, F, D, hydroxy, NH$_2$, a (C$_1$ to C$_{10}$) alkoxy, a substituted or unsubstituted (C$_1$ to C$_{30}$) alkyl, a substituted or unsubstituted (C$_2$ to C$_{30}$) alkenyl, a substituted or unsubstituted (C$_2$ to C$_{30}$) alkynyl, a substituted or unsubstituted (C$_3$ to C$_{30}$) cycloalkyl, a substituted or unsubstituted (C$_3$ to C$_{30}$) cycloalkenyl, a substituted or unsubstituted (C$_8$ to C$_{30}$) cycloalkynyl, a substituted or unsubstituted —N-linked amido, —(C=O)L or —O(C=O)R$^5$, wherein —(C=O)L is a hydrolyzable prodrug ester leaving group; or
$R^1$ is H, —CH$_3$, —CF$_3$, or a substituted or unsubstituted (C$_2$ to C$_5$) alkyl;
$R^2$ is H;
$R^3$ is H, D, a (C$_1$ to C$_{10}$) alkoxy, a substituted (C$_1$ to C$_{30}$) alkyl, an unsubstituted (C$_2$ to C$_{30}$) alkyl, a substituted or unsubstituted (C$_2$ to C$_{30}$) alkenyl, a substituted or unsubstituted (C$_2$ to C$_{30}$) alkynyl, a substituted or unsubstituted (C$_3$ to C$_{30}$) cycloalkyl, a substituted or unsubstituted (C$_3$ to C$_{30}$) cycloalkenyl, a substituted or unsubstituted (C$_8$ to C$_{30}$) cycloalkynyl, a substituted or unsubstituted —N-linked amido or —O(C=O)R$^5$;
$R^4$ is a substituted or unsubstituted (C$_1$ to C$_{10}$) alkyl;
$R^5$ is a substituted or unsubstituted (C$_1$ to C$_6$) alkyl, a substituted or unsubstituted aryl(C$_{1-6}$ alkyl) or

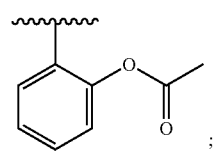 [SMILES: *c1ccccc1OC(C)=O] ;

and
Y is S or O; and
with the proviso that when R$^3$ hydrogen, then R$^1$ and R$^2$ cannot both be hydrogen.

42. The compound of claim 41, wherein R$^2$ is —C(=Y)R$^4$.
43. The compound of claim 42, wherein Y is O.
44. The compound of claim 42, wherein Y is S.
45. The compound of claim 41, wherein R$^4$ is a substituted or unsubstituted (C$_1$ to C$_{10}$) alkyl.
46. The compound of claim 41, wherein R$^2$ is H.
47. The compound of claim 41, wherein R$^1$ is H.
48. The compound of claim 41, wherein R$^1$ is —CH$_3$.
49. The compound of claim 41, wherein R$^1$ is —CF$_3$.
50. The compound of claim 41, wherein R$^1$ is a substituted or unsubstituted (C$_2$ to C$_5$) alkyl.
51. The compound of claim 41, wherein R$^3$ is H.
52. The compound of claim 41, wherein R$^3$ is D.
53. The compound of claim 41, wherein R$^3$ is a (C$_1$ to C$_{10}$) alkoxy.
54. The compound of claim 41, wherein R$^3$ is a substituted or unsubstituted (C$_2$ to C$_{30}$) alkyl.
55. The compound of claim 41, wherein R$^3$ is a substituted or unsubstituted (C$_2$ to C$_{30}$) alkenyl.
56. The compound of claim 41, wherein R$^3$ is a substituted or unsubstituted (C$_2$ to C$_{30}$) alkynyl.
57. The compound of claim 41, wherein R$^3$ is a substituted or unsubstituted (C$_3$ to C$_{30}$) cycloalkyl.
58. The compound of claim 41, wherein R$^3$ is a substituted or unsubstituted (C$_3$ to C$_{30}$) cycloalkenyl.
59. The compound of claim 41, wherein R$^3$ is a substituted or unsubstituted (C$_8$ to C$_{30}$) cycloalkynyl.
60. The compound of claim 41, wherein R$^3$ is a substituted (C$_6$ to C$_{30}$) aryl.
61. The compound of claim 41, wherein R$^3$ is an unsubstituted (C$_7$ to C$_{30}$) aryl.
62. The compound of claim 41, wherein R$^3$ is a substituted or unsubstituted heteroaryl.
63. The compound of claim 41, wherein R$^3$ is a substituted or unsubstituted heterocyclyl.
64. The compound of claim 41, wherein R$^3$ is a substituted or unsubstituted aryl(C$_{1-6}$ alkyl).
65. The compound of claim 41, wherein R$^3$ is a substituted or unsubstituted heteroaryl(C$_{1-6}$ alkyl).
66. The compound of claim 41, wherein R$^3$ is a substituted or unsubstituted —N-linked amido.

67. The compound of claim 41, wherein $R^3$ is —O(C=O)$R^5$.
68. The compound of claim 67, wherein $R^5$ is a substituted or unsubstituted ($C_1$ to $C_6$) alkyl.
69. The compound of claim 67, wherein $R^5$ is a substituted or unsubstituted aryl($C_{1-6}$ alkyl).
70. The compound of claim 67, wherein $R^5$ is
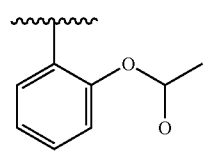
71. The compound of claim 41, wherein the compound is selected from the group consisting of:
1
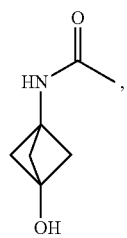
2
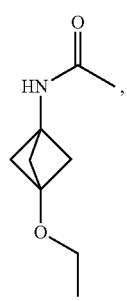
3
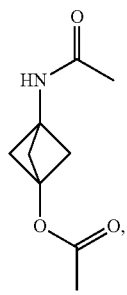
4
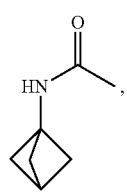
-continued
5
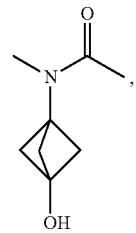
6
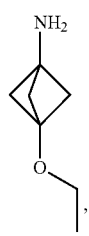
7
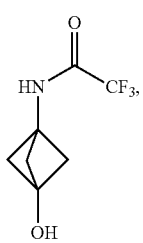
8
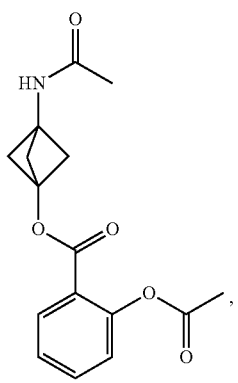
9
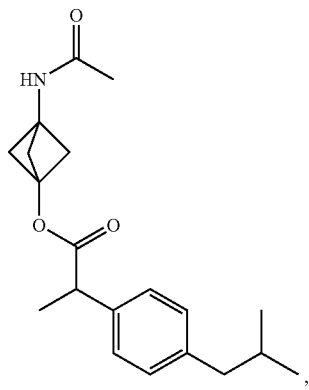

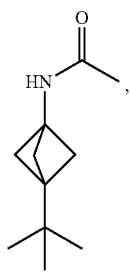
10
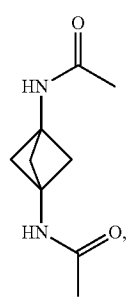
11
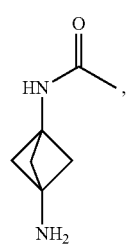
12
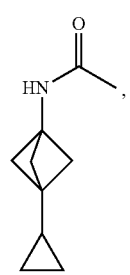
13
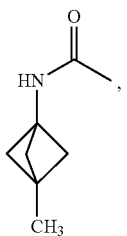
10
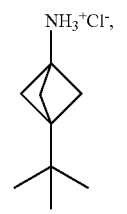
11
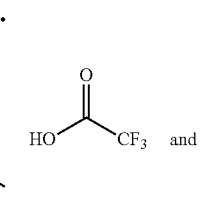
12
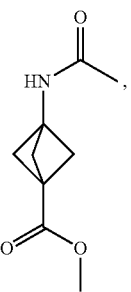
13
or a pharmaceutically acceptable salt of the foregoing.
72. A pharmaceutical composition comprising an effective amount of a compound of claim 41, or a pharmaceutically acceptable salt thereof, and a pharmaceutically acceptable carrier, diluent, excipient or combination thereof.
73. The method of claim 10 wherein $R^4$ is $CF_3$.
74. The method of claim 14, wherein $R^1$ is $CF_3$.
* * * * *

UNITED STATES PATENT AND TRADEMARK OFFICE
CERTIFICATE OF CORRECTION

PATENT NO.       : 9,447,026 B2
APPLICATION NO.  : 14/439636
DATED            : September 20, 2016
INVENTOR(S)      : Kevin Duane Bunker It is certified that error appears in the above-identified patent and that said Letters Patent is hereby corrected as shown below:

On the Title Page

In Column 2 (page 2, item (56)) at Line 8, Under Other Publications, change "admantyl" to --adamantyl--.

In the Specification

In Column 4 at Line 48, Change "thiopheneylethyl," to --thiophenylethyl,--.

In Column 5 at Lines 12-13 (approx.), Change "pivoyloxymethyl," to --pivaloyloxymethyl,--.

In Column 15 at Line 12, Change "Amone" to --Arnone--.

In Column 19 at Line 7, Change "tartarate," to --tartrate,--.

In the Claims

In Column 34 at Line 65 (approx.), In Claim 1, change "$C_m$)" to --$C_{10}$)--.

Signed and Sealed this
Third Day of January, 2017

Michelle K. Lee
*Director of the United States Patent and Trademark Office*